(12) United States Patent
Arias et al.

(10) Patent No.: US 11,127,932 B2
(45) Date of Patent: Sep. 21, 2021

(54) SIMULTANEOUS DOCTOR BLADING OF DIFFERENT COLORED LIGHT EMITTING COMPONENTS

(71) Applicant: The Regents of the University of California, Oakland, CA (US)

(72) Inventors: Ana Claudia Arias, Lafayette, CA (US); Donggeon Han, Berkeley, CA (US); Claire Meyer Lochner, Berkeley, CA (US); Adrien Pierre, Berkeley, CA (US)

(73) Assignee: The Regents of the University of California, Oakland, CA (US)

( * ) Notice: Subject to any disclaimer, the term of this patent is extended or adjusted under 35 U.S.C. 154(b) by 1 day.

(21) Appl. No.: 16/559,264

(22) Filed: Sep. 3, 2019

(65) Prior Publication Data
US 2020/0006713 A1 Jan. 2, 2020

Related U.S. Application Data

(63) Continuation of application No. PCT/US2018/020623, filed on Mar. 2, 2018.
(Continued)

(51) Int. Cl.
| | |
|---|---|
| *H01L 51/56* | (2006.01) |
| *H01L 51/00* | (2006.01) |
| *A61B 5/024* | (2006.01) |
| *A61B 5/1455* | (2006.01) |
| *H01L 51/50* | (2006.01) |

(52) U.S. Cl.
CPC .......... *H01L 51/56* (2013.01); *H01L 51/0004* (2013.01); *H01L 51/0012* (2013.01);
(Continued)

(58) Field of Classification Search
CPC . H01L 51/56; H01L 51/0004; H01L 51/0012; H01L 51/0097; H01L 51/5012;
(Continued)

(56) References Cited

U.S. PATENT DOCUMENTS

| | | |
|---|---|---|
| 4,366,754 A | 1/1983 | Sarda |
| 6,936,102 B1 | 8/2005 | Otsuki et al. |

(Continued)

OTHER PUBLICATIONS

Han et al.; Flexible Blade-Coated Multicolor Polymer Light-Emitting Diodes for Optoelectronic Sensors; 2017, Advanced Materials; 2017, 29, 1606206 (Year: 2017).*

(Continued)

*Primary Examiner* — Syed I Gheyas
(74) *Attorney, Agent, or Firm* — Leydig, Voit & Mayer, Ltd.; Gerald T. Gray

(57) ABSTRACT

Methods for simultaneously forming two or more different colored material layers on a substrate. include performing surface energy patterning (SEP) to define a first, hydrophobic region and a second, hydrophilic region on the substrate, applying first and second materials on the second region, wherein the first material comprises a material having a first color, and wherein the second material comprises a material having a second color, and doctor blade coating the first and second materials simultaneously to form first and second material layers on the substrate. The methods are particularly useful for making multi-color light emitting and detecting components such as LEDs and OPDs.

20 Claims, 18 Drawing Sheets

Related U.S. Application Data

(60) Provisional application No. 62/466,144, filed on Mar. 2, 2017.

(52) U.S. Cl.
CPC ...... *H01L 51/0097* (2013.01); *A61B 5/02416* (2013.01); *A61B 5/14551* (2013.01); *H01L 51/5012* (2013.01); *H01L 2251/5338* (2013.01)

(58) Field of Classification Search
CPC . H01L 2251/5338; H01L 51/50; H01L 51/52; H01L 51/0014; H01L 51/0003
See application file for complete search history.

(56) References Cited

U.S. PATENT DOCUMENTS

| | | |
|---|---|---|
| 10,548,519 B2 | 2/2020 | Arias et al. |
| 2003/0230967 A1 | 12/2003 | Kawamura et al. |
| 2005/0230678 A1* | 10/2005 | Cao ..................... H01L 51/5212 257/40 |
| 2005/0242341 A1 | 11/2005 | Knudson et al. |
| 2006/0131563 A1* | 6/2006 | Salleo ..................... H01L 27/28 257/40 |
| 2010/0203235 A1 | 8/2010 | Verschuuren et al. |
| 2012/0229709 A1 | 9/2012 | Heald et al. |
| 2013/0285026 A1* | 10/2013 | Miskiewicz ............ C08L 65/00 257/40 |
| 2018/0116525 A1 | 5/2018 | Lochner et al. |

OTHER PUBLICATIONS

International Search Report in International Patent Application No. PCT/US2018/020623 dated May 1, 2018.
Han et al., "Flexible Blade-Coated Multicolor Polymer Light-Emitting Diodes for Optoelectronic Sensors," Advanced Materials, vol. 29, Issue 22, Apr. 10, 2017.

* cited by examiner

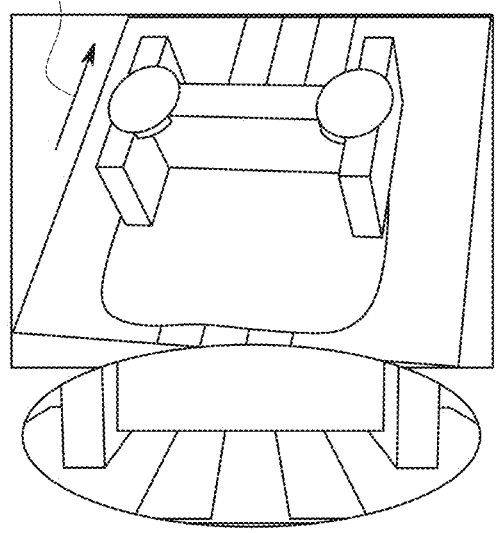
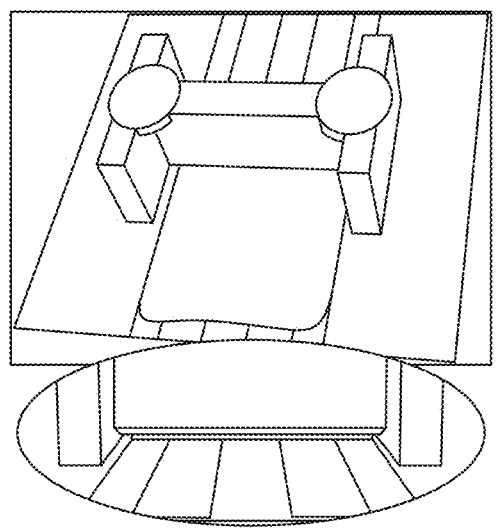
FIG. 6A  FIG. 6B
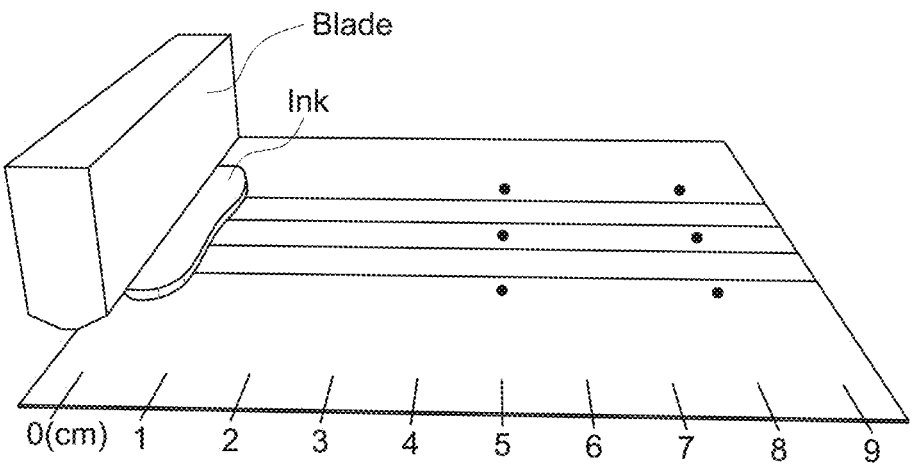
FIG. 7

SIMULTANEOUS DOCTOR BLADING OF DIFFERENT COLORED LIGHT EMITTING COMPONENTS

CROSS-REFERENCE TO RELATED APPLICATIONS

This Patent Application is a continuation of PCT Application No. PCT/US2018/020623 by Arias et al., entitled "SIMULTANEOUS DOCTOR BLADING OF DIFFERENT COLORED LIGHT EMITTING COMPONENTS," filed Mar. 2, 2018, which claims priority to U.S. Provisional Patent Application No. 62/466,144 by Arias et al., entitled "SIMULTANEOUS DOCTOR BLADING OF DIFFERENT COLORED ORGANIC LIGHT EMITTING DIODES," filed Mar. 2, 2017, each of which is incorporated herein by reference in its entirety.

BACKGROUND

The present disclosure generally provides systems and methods for forming optical devices and in particular to forming optical devices including two or more different colored polymer light emitting devices.

Organic light-emitting diodes (OLEDs) have changed the conventional paradigm of light-emitting devices and are driving innovations in optoelectronic technologies and applications. The fact that OLEDs can be made flexible makes them suitable for diverse usage, including wearable electronics. Indeed, OLEDs have gone beyond flexible; now it is possible to stretch and crumple them, which makes OLEDs even more unique than their solid-state counterparts. On par with the investment and interest, researchers have investigated OLEDs in numerous contexts, and research on solution processable polymer light-emitting diodes (PLEDs) is no exception. One of the primary advantages of OLEDs such as PLEDs is that they can be fabricated with printing techniques. Printing OLEDs allows for reduced material consumption, low-cost mass-production, and simplified fabrication procedures as compared to conventional evaporated OLEDs or spin-coated PLEDs. Adopting printing schemes into the fabrication of OLED displays is considered crucial in industries to improve the cost competitiveness against conventional display technologies. Also, the merits of printing OLEDs allow them to be potentially disposable, which provides numerous new opportunities. Disposable medical devices that require light sources can largely benefit by utilizing OLEDs instead of solid-state LEDs as the lifetime requirements for these devices are not as stringent as consumer electronics. Additionally, in wearable sensing scenarios, flexible devices enhance the signal-to-noise ratio (SNR) by conforming to the skin. Due to the flexible form factor, OLEDs provide the same advantage of improved SNR by establishing a high-fidelity sensor-skin interface that improves light coupling to the skin and reduces ambient noise.

To date, several printing techniques have been introduced for PLED fabrication. Inkjet printing allows selective deposition of different kinds of polymers by controlling the ink drop rate and the substrate surface energy, which makes it a promising choice for the next generation deposition technology in display industries. Slot-die coating is another printing technique, which can provide large area homogeneous films, and has been previously used for organic photovoltaics (OPVs) and PLEDs. Other printing methods that have been used in electronics are screen printing, gravure printing and blade-coating. Among these techniques, blade-coating is especially attractive in that the blade does not directly contact the target surface, is relatively simple to configure, has high throughput, consumes low amount of material, and provides thickness control of the deposited material by tuning coating parameters. Blade coating techniques have also been previously used to fabricate all-printed organic thin-film transistors (OTFTs) and organic photodiodes (OPDs). One of the problems with blade-coating is that the deposited film may demonstrate non-uniform thickness along the blade coating direction. It has been shown that it is possible to control the uniformity of the thickness by blowing hot air over the target area or by using a modified blade-coating system, where a slit is placed in front of the blade to provide a uniform amount of solution to the blade.

For both display and sensing systems with LEDs, having a variety of colors is crucial. In LED displays, three fundamental colors, red, green and blue, are used to generate all other derivative colors. In sensing systems, having multiple wavelengths broadens the extent of applications by allowing for ratiometric measurements. For example, in pulse oximetry, using a single color enables only photoplethysmogram (PPG) measurements. On the other hand, two colors, red and green, enable pulse oxygenation measurement via ratiometric sensing. The deposition of multicolor LEDs with a monolithic process, on a single substrate, reduces process steps and simplifies system integration. High resolution printing techniques have been previously used to demonstrate full color displays. However depositing multiple active materials with high throughput and simple coating techniques, such as blade coating, remains a challenge. More specifically, for PLEDs, only a single color PLED per substrate has been demonstrated, limiting the usage to single-color applications.

Recently, spin-coated PLEDs have been used to measure pulse and oxygenation, demonstrating that they can be used for optoelectronic sensing. Red and green PLEDs, which were fabricated on separate substrates, were coupled with an organic photodiode to perform photoplethysmogram (PPG) measurements. Furthermore, the oxygenation measurement was performed using transmission of light through fingertips. The transmission-mode measurement technique limits the sensing locations to the extremities of the body, where light can travel through the skin and tissue. In the reflection-mode sensing scheme, light emitters and detectors remain on the same side of the skin and acquire the PPG signal via reflected light. With reflection-mode sensing, it is possible to go beyond conventional sensing locations. Moreover, to truly realize the full potential of OLEDs in medical applications such as pulse oximetry, it is ideal to use a high-throughput manufacturing scheme, such as blade coating, to fabricate the OLEDs.

SUMMARY

The present disclosure provides embodiments for forming multiple color devices, or multiple materials, on the same substrate using a doctor blade process.

According to an embodiment, a method is provided for simultaneously forming two or more different colored material layers on a substrate. The method typically includes performing surface energy patterning to define a first region and a second region on the substrate, wherein the first region is hydrophobic and the second region is hydrophilic, applying first and second materials on the second region, wherein the first material comprises a material having a first color, and wherein the second material comprises a material having a second color, and doctor blade coating the first and second materials simultaneously to form first and second material layers on the substrate. In certain aspects the substrate includes a flexible substrate. In certain aspects, the method further includes depositing a pattern of a first conductive material on the substrate prior to performing the surface energy patterning, whereby the first and second regions comprise at least a portion of the first conductive material.

According to another embodiment, a method of forming multi-color devices on a substrate is provided. The devices may include organic light emitting devices, such as organic light-emitting diodes, and/or organic light detection devices, such as organic photodetectors. The method typically includes depositing a pattern of a first conductive material on a flexible substrate, performing surface energy patterning to define a first region and a second region on the flexible substrate and/or the first conductive material, wherein the first region is hydrophobic and the second region is hydrophilic, applying first and second materials on the second region, and doctor blade coating the first and second materials simultaneously to form first and second material layers on the flexible substrate. In certain aspects, the method includes positioning a flexible substrate material on a rigid carrier before the step of applying. In certain aspects, the first and second material layers define first and second organic light-emitting diodes (OLEDs), respectively. In certain aspects, the first and second material layers define first and second polymer light-emitting diodes (PLEDs), respectively. In certain aspects, at least one of the first and second material layers defines an organic photodetector device. In certain aspects, the flexible substrate comprises polyethylene naphthalate (PEN). In certain aspects, the first conductive material comprises indium tin oxide (ITO). In certain aspects, the performing surface energy patterning includes applying a hydrophobic self-assembling monolayer (SAM) to the flexible substrate, applying an etch barrier material to define a pattern on the SAM layer, etching the SAM layer to define the first region and the second region, and removing the etch barrier material. In certain aspects, the etch barrier material comprises kapton tape. In certain aspects, the etching comprises an oxygen plasma etch. In certain aspects, the second region comprises at least two separated portions. In certain aspects, the applying first and second materials on the second region includes applying the first material on a first portion of the second region and applying the second material on a second portion of the second region different that the first portion of the second region, whereby the first and second material layers overlay different portions of the flexible substrate.

In certain aspects, doctor blade coating is performed using a blade coating assembly including a single blade for blading both the first and second materials. In certain aspects, doctor blade coating is performed using a blade coating assembly including a separate blade for each of the first and second materials. In certain aspects multiple blades, each configured to blade one or more materials may be used.

Reference to the remaining portions of the specification, including the drawings and claims, will realize other features and advantages of the present invention. Further features and advantages of the present invention, as well as the structure and operation of various embodiments of the present invention, are described in detail below with respect to the accompanying drawings. In the drawings, like reference numbers indicate identical or functionally similar elements.

BRIEF DESCRIPTION OF THE SEVERAL VIEWS OF THE DRAWING(S)

The detailed description is described with reference to the accompanying Figures. The use of the same reference numbers in different instances in the description and the Figures may indicate similar or identical items.

FIGS. 1b and 1c illustrate embodiments of OLED structures for single color OLEDs and multicolor OLEDs, respectively.

FIG. 2 illustrates device performance of single color (green, red, and NIR) PLEDs on PEN/ITO. FIG. 2a shows current-density-voltage-radiance characteristics; FIG. 2b shows total flux vs current-density; FIG. 2c shows external quantum efficiency vs radiance; FIG. 2d shows Power efficiency (mWW$^{-1}$) vs radiance of each device. The inset in (b): normalized electroluminescence (EL) spectra of the three colors.

FIG. 3 illustrates device performance of multicolor PLEDs (green and red) on PEN/ITO. FIG. 3a) shows current-density-voltage-luminance characteristics; FIG. 3b shows total flux vs current-density; FIG. 3c shows external quantum efficiency vs luminance; FIG. 3d shows power efficiency (lmW$^{-1}$) vs luminance of each device. The inset in (b): normalized EL spectra of the two colors. The inset in (c): photograph of multicolor PLEDs in operation at 6V.

FIG. 4 illustrates a system design and PLED specifications for obtaining photoplethysmogram (PPG) signal from the wrist of a user/wearer. FIG. 4a shows a schematic illustration of the system setup for acquiring the PPG signal. An optoelectronic probe composed of green and red PLEDs, and a silicon PD are placed on top of the wrist. The PLEDs and the PD are controlled using an analog front end (AFE). The AFE filters and amplifies the PD signal and sends to a microcontroller (μC) over serial peripheral interface (SPI) bus. The processed signal is then sent to a computer using a universal serial bus (USB). FIG. 4b shows signal amplifications using the AFE. In the first stage (Gain 1), both the AC and DC parts are amplified, whereas in the second stage (Gain 2) only the AC part of the signal is amplified. FIG. 4c shows pulse signal from green, red, and NIR PLEDs for different PLED current densities. Current densities of 1, 2, 4, and 10 mAcm$^{-2}$ are used for all the PLEDs. The bars show the pulse signal magnitudes (the error bars represent the standard deviation of the data collected for 3 separate runs). At 10 mAcm$^{-2}$ current density, reproducible pulse signal are obtained from all the three colors. FIGS. 4d, 4f show PPG signal and detected heartbeat peaks from the PPG signal from green, red, and NIR PLEDs, respectively at 10 mAcm$^{-2}$ current density. The top panels show the PPG signal, and the bottom panels show the detected heartbeats using a peak detection algorithm.

Figure 5A:
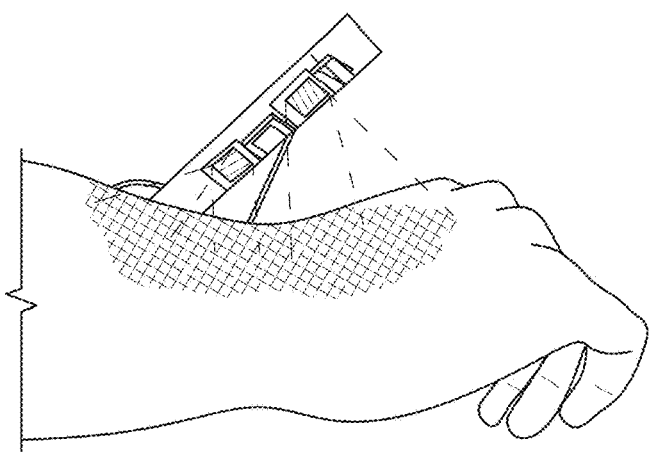
Figure 5B:
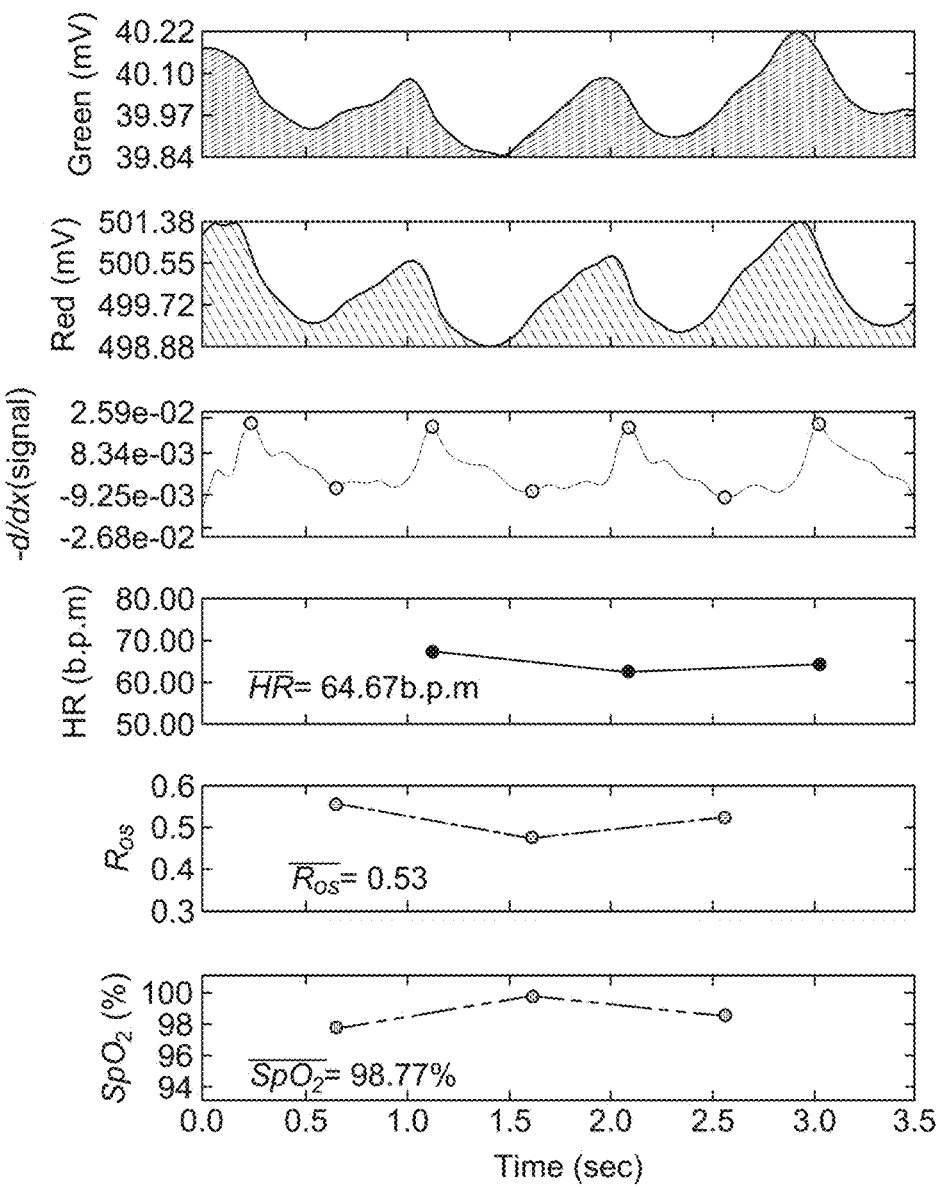

FIG. 5 illustrates reflection-mode pulse oximetry using green and red PLEDs, and a silicon PD on a wearer's wrist. FIG. 5a is a photograph of the optoelectronic sensor that uses green and red PLEDs as the light source and a silicon PD as the light detector (the sensor is placed on top of the wrist for collecting the PPG signal). FIG. 5b shows reflection-mode pulse oximetry results. The top two panels (green and red) show the PPG signal from the green and red PLEDs, respectively. Panel 3 shows heartbeat peaks (blue dots) and valleys (red dots) detected from the PPG signals. Panel 4 shows the detected heart rate (HR) in beats per minute (b.p.m.) by timing the heartbeat peaks (blue dots in panel 3). The ratio of the red and green signals, $R_{os}$ and calculated oxygen saturation $S_pO_2$ are shown in the bottom two panels using orange and purple colors, respectively. Average oxygen saturation $S_pO_2$ of 98.77% is observed using an empirical correction to Beer-Lambert's law.

FIG. 6a and FIG. 6b illustrate the blade coating process according to an embodiment: without the SEP, coated film is dispersed widely on the substrate and ink is spread beyond the blade support; and with the SEP, coated film as well as the ink underneath the blade is confined between the hydrophobic region (yellow), respectively.

FIG. 7 illustrates a blade-coating setup with position markers to help understanding of Tables S1 and S2.

FIG. 8 shows surface analysis of blade-coated PEDOT: PSS film: FIG. 8a shows a 3×3 μm AFM image of PEDOT: PSS printed on glass substrate. The characterized area has peak-to-peak roughness of 7.3 nm. FIGS. 8b-d show optical profiler images of PEDOT:PSS printed on PEN/ITO. FIG. 8b shows a 643×643 μm image of defect free region. The profiled region displays peak-to-peak roughness of 9 nm. FIG. 8c shows a 129×130 μm image of a defect with profile of the defect. The defect is round shaped with a diameter of 5 μm. FIG. 8d shows the same image with profile near the defect. The profile near the defect has peak-to-peak roughness of 9 nm. Red lines in the figures indicate the location of the profile.

Figure 9A:
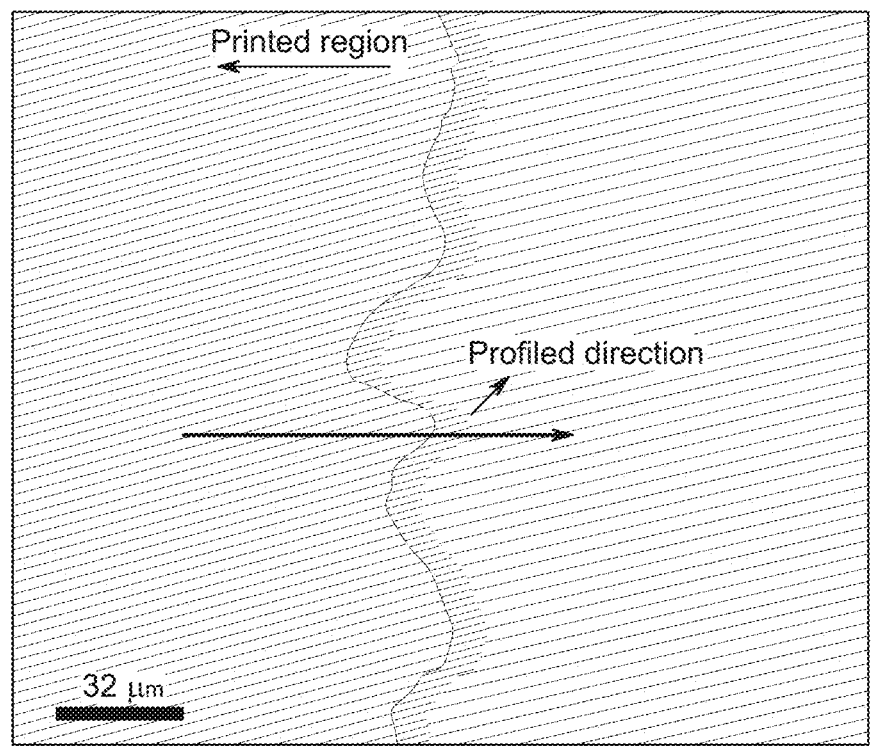

FIG. 9a shows an optical microscopic image of printed PEDOT:PSS edge. The red line indicates where the edge was profiled.

Figure 9B:
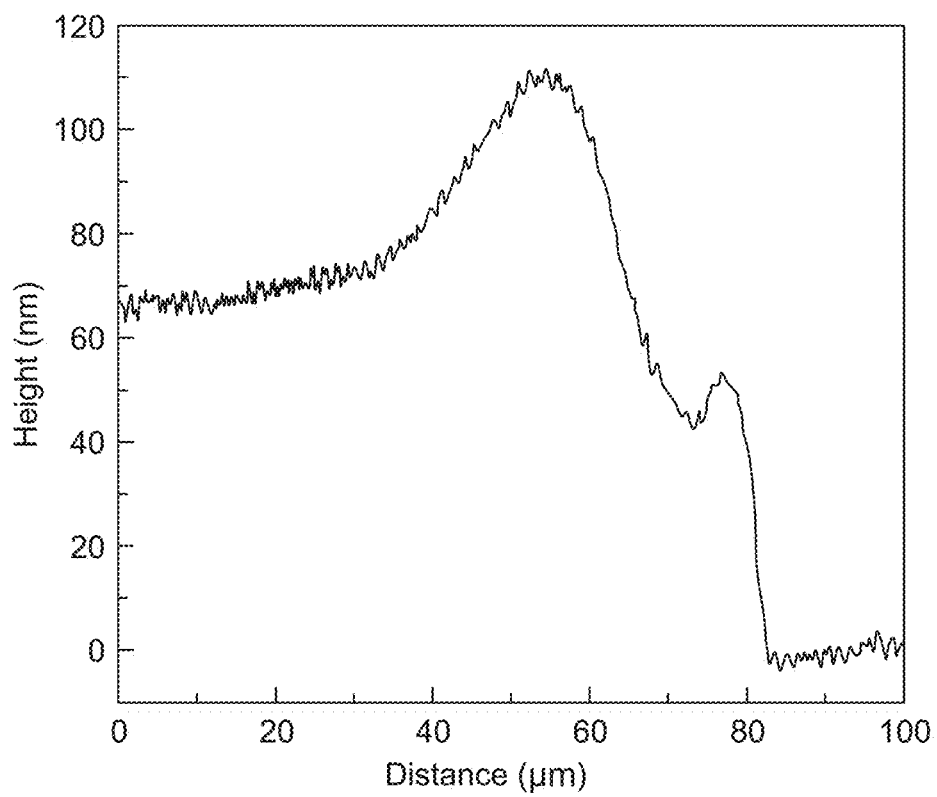

FIG. 9b shows PEDOT:PSS edge profiled with Dektak. The edge has 40 μm wide hill that is about 40 nm high before it reaches a constant thickness of 70 nm.

Figure 10:
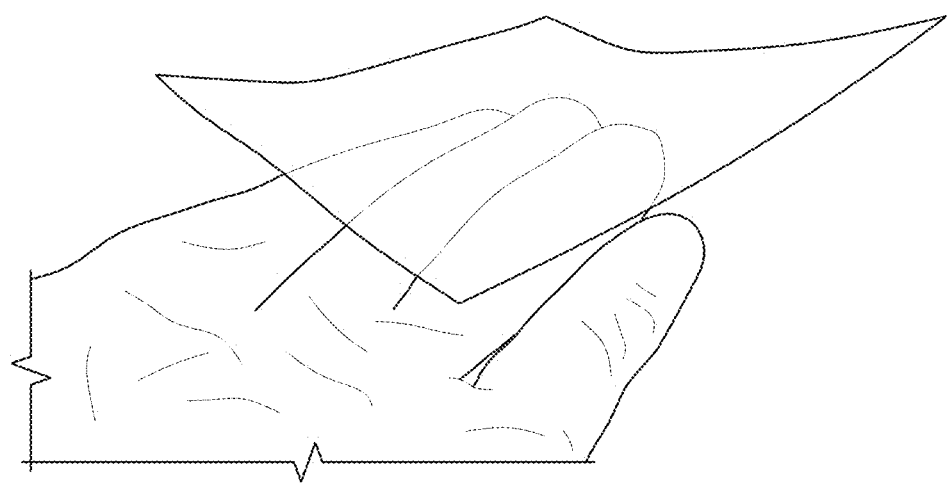

FIG. 10 shows a photograph of a deformed 10 cm×10 cm PEN/ITO substrate after 180° C. annealing.

Figure 11:
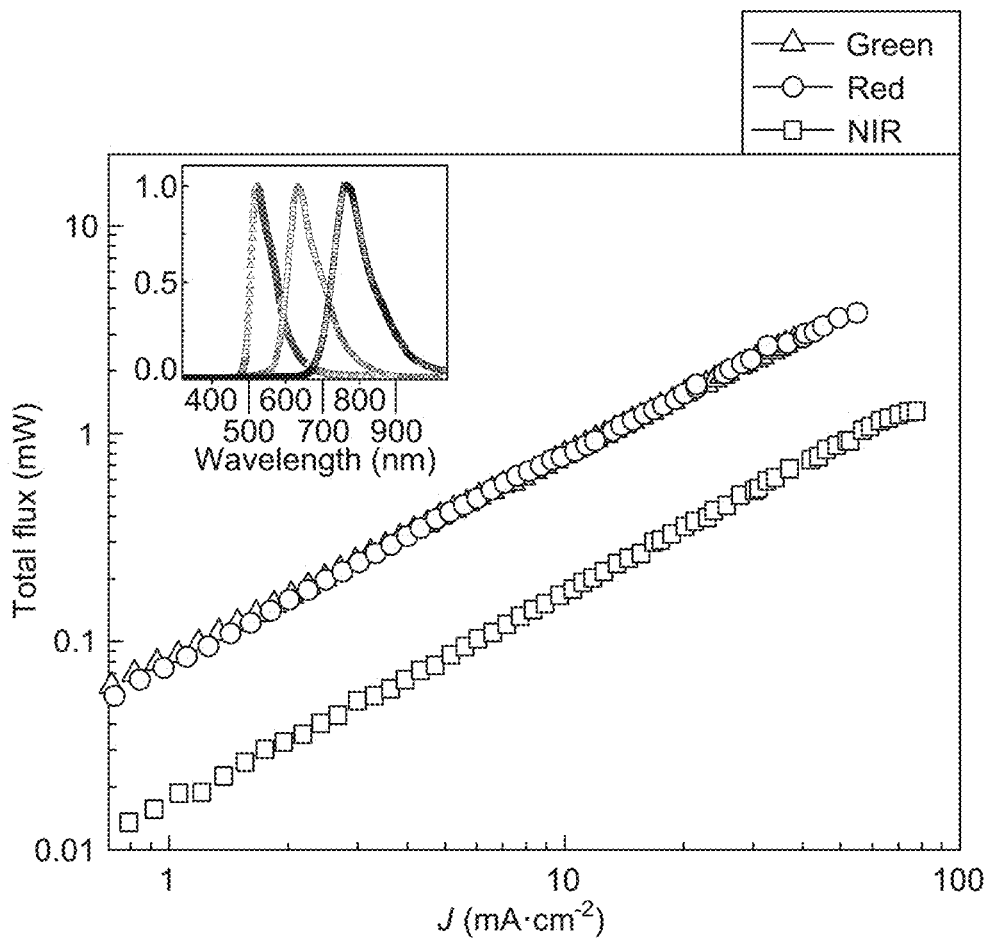

FIG. 11 shows total flux vs current-density of single color PLEDs after PPG measurement on the wrist. Inset:normalized emission spectrum of the three colors.

Figure 12:
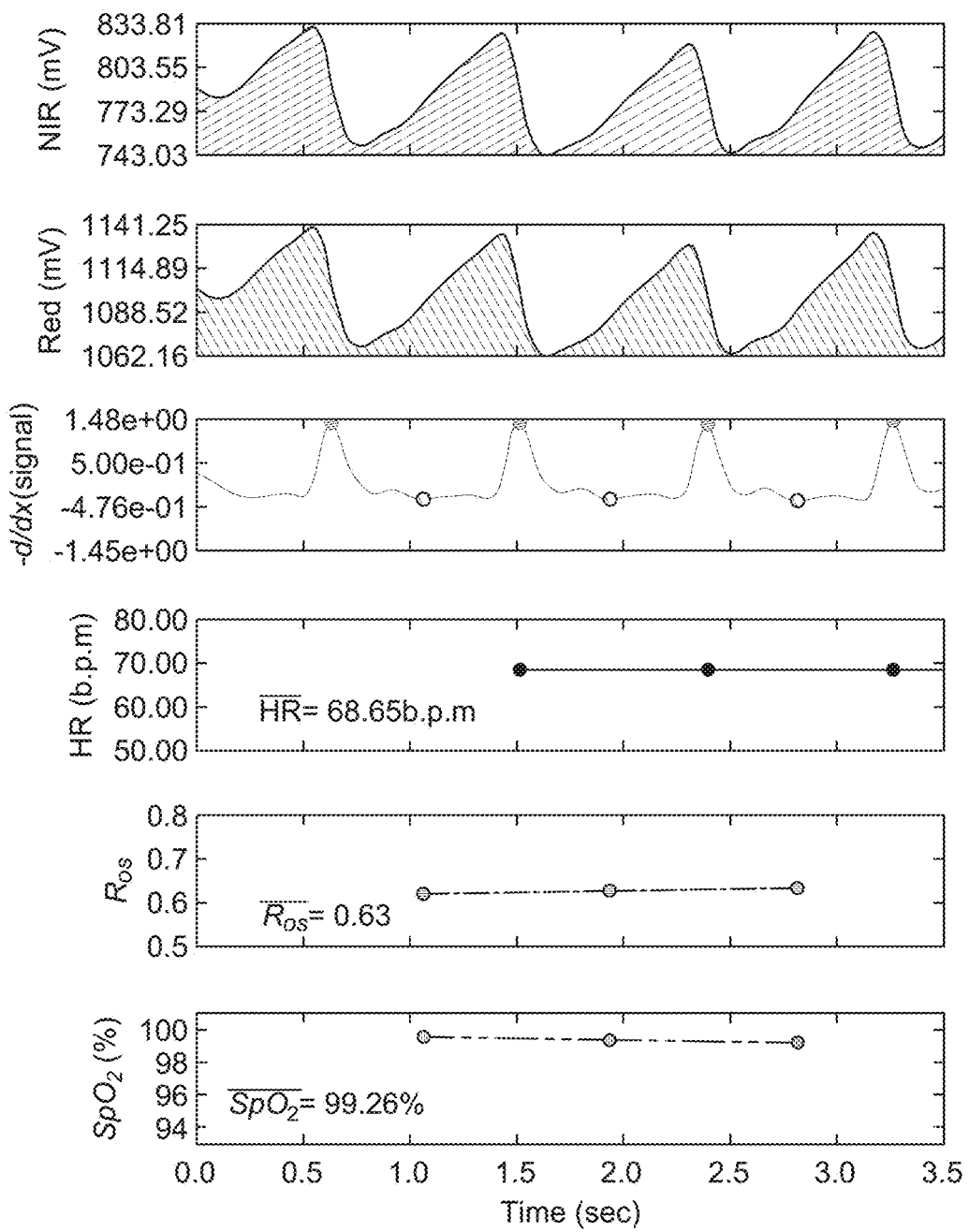

FIG. 12 shows transmission-mode pulse oximetry using commercially available pulse oximetry probe consisting of red and NIR light-emitting diodes (LEDs) and a silicon PD. The top two panels (gray and red) show the PPG signal from the NIR and red LEDs, respectively. Panel 3 shows heartbeat peaks (blue dots) and valleys (red dots) detected from the PPG signals. Panel 4 shows the detected heart rate (HR) in beats per minute (b.p.m.) by timing the heartbeat peaks (blue dots in panel 3). The ratio of the red and NIR signals, Ros and calculated oxygen saturation SpO2 are shown in the bottom two panels using orange and purple colors, respectively. The commercial device in transmission mode recorded an average oxygen saturation SpO2 of 99.26% compared to the reflection-mode probe composed of red and green PLEDs, which recorded an average oxygen saturation SpO2 of 98.77%.

DETAILED DESCRIPTION

The present disclosure provides embodiments for forming multiple colors, or multiple materials on the same substrate. The present embodiments are particularly advantageous for forming multiple LEDs of differing colors in the same substrate. In certain embodiments, multicolor blade-coated OLEDs are fabricated on a flexible substrate designed to perform reflection-mode pulse oximetry on the wrist. In certain embodiments, the blade-coating area is designated by surface energy patterning (SEP). SEP has previously been used for OTFTs to print the source and drain with PEDOT:PSS in desired patterns. Green, red, and near-infrared (NIR) OLEDs, including PLEDs, are used for PPG embodiments as these colors are capable of executing PPG measurements.

SEP is used to define regions to print two colors on one substrate and to demonstrate multicolor blade-coated OLEDs, the performance of which is similar to the single-color OLEDs. Blade-coated single-color OLEDs are characterized—power efficiencies of 31.2, 42.7, and 8.6 mWW$^{-1}$ for green, red, and NIR, respectively at 1 Wsr$^{-1}$m$^{-2}$ are obtained. All devices were stable throughout the full characterization process and showed uniform light emission in the active area of 0.49 cm$^2$. For blade-coated multi-color OLEDs on a substrate, at 1000 cdm$^{-2}$, luminous efficacies of 12.2 and 8 lmW$^{-1}$ for green and red are obtained, respectively. For demonstrating reflection-mode PPG measurements in conjunction with a silicon photodiode (PD), the operating condition of the OLEDs is tuned to provide adequate flux for measuring the PPG signal at the wrist. A number of factors can influence the PPG signal, such as the wavelength of the light, the intensity of the light, and geometry of the device. OLED operating current-density ($J_{op}$) of 10 mAcm$^{-2}$ resulted in 0.68, 0.89, and 0.19 mW of flux which provided 1.1, 1.0, and 1.2 mV PPG signals for green, red and NIR OLEDs, respectively. Light absorption in the tissue depends on the wavelength of the light; therefore, PPG signal attenuation of visible light is more pronounced than that of NIR light. The spacing between two OLEDs is designed so that a photodiode can be placed in between the OLEDs. Finally, with the fabricated multicolor OLEDs and a silicon PD, reflection-mode PPG measurements on a subject's wrist were performed to accurately record pulse and oxygenation values, which are confirmed by a commercially available transmission-mode pulse oximeter that is used on the index finger. In certain embodiments, organic photodetectors (OPDs) are also constructed according to the embodiments herein.

Figure 1A:
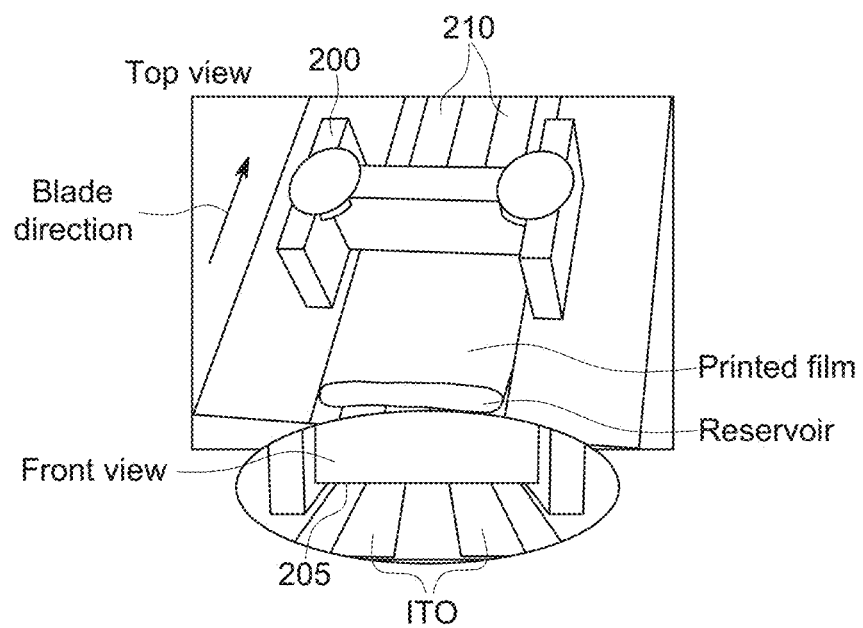
FIGS. 1a and 1b illustrate a top and front view of embodiments of a blade-coating process using SEP for single color OLEDs and multicolor OLEDs, respectively.
Figure 1B:
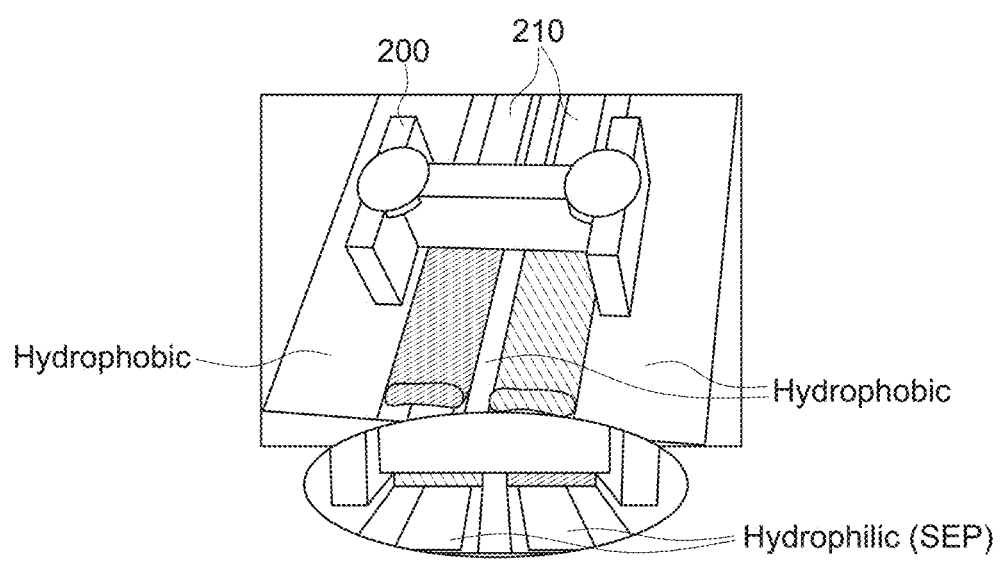
Figure 1C:
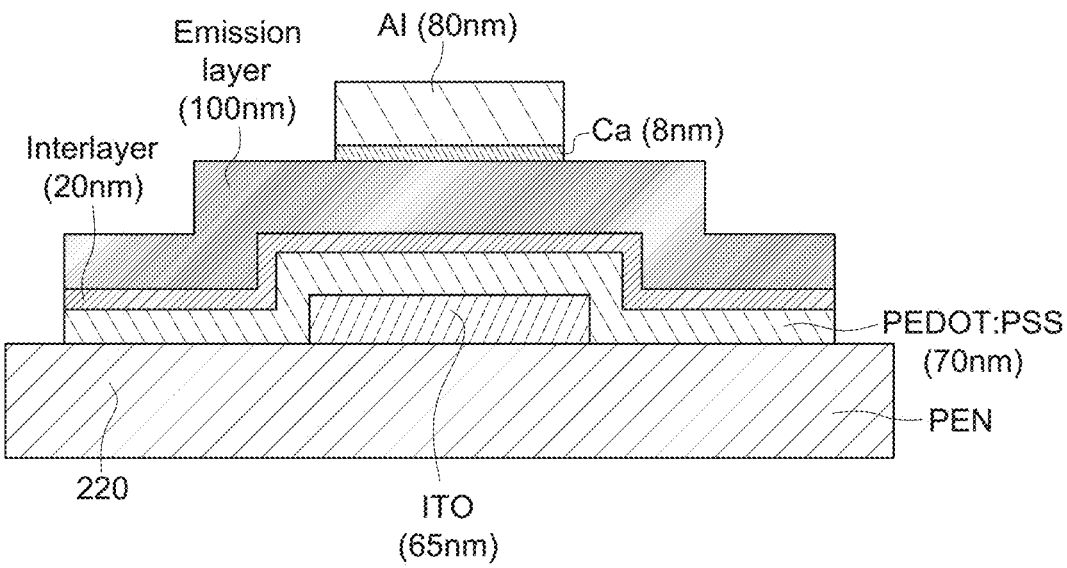
Figure 1D:
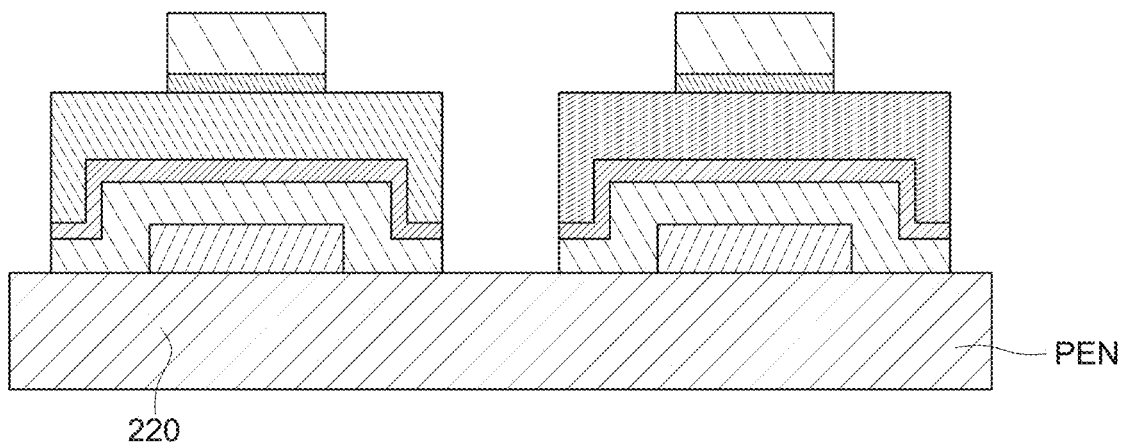
Figure 1E:
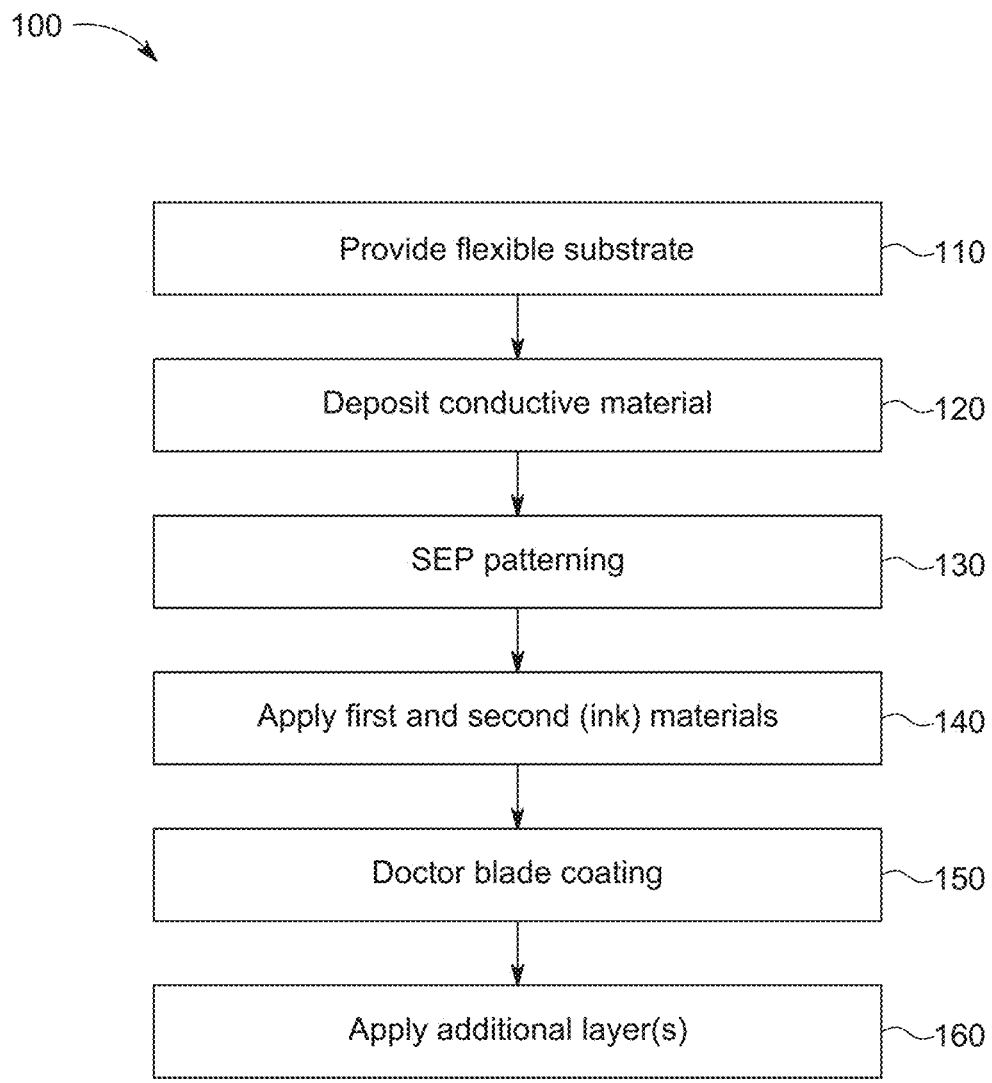
FIG. 1e shows a method for simultaneously forming two (or more) different color ink layers on a flexible substrate according to an embodiment.

FIG. 1e shows a method 100 for simultaneously forming two (or more) different color ink layers on a flexible substrate according to an embodiment. The method 100 may be used to form multi-color light-emitting devices, such as two or more OLEDs on a flexible substrate. In step 110, a flexible substrate is provided. Useful substrate materials include PEN (polyethylene naphthalate), PET (polyethylene terephthalate), PI (polyimide), PEI (polyetherimide), PTFE (polytetrafluoroethylene), PAEK (polyaryletherketone), (PES) Polyethersulphone, PEEK (poly ether ketone), foil or paper. The substrate may optionally be positioned or affixed to a rigid carrier. In step 120, a pattern of a first conductive material is deposited on the flexible substrate. An example of a useful conductive material is ITO, although other materials may be used, such as thin metal films and conductive polymers, e.g., PEDOT:PSS (Poly(3,4-ethylenedioxythiophene)-poly(styrenesulfonate)).

This patterning step 120 may be performed using known techniques. In step 130, surface energy patterning (SEP) is performed to define hydrophobic and hydrophilic regions on the substrate. For example, to form two different device components, SEP may be performed to form a first region and a second region on the flexible substrate, wherein the first region is hydrophobic and the second region is hydrophilic. SEP may be performed, for example, using an oxygen plasma with a mask to define regions (e.g., hydrophilic and hydrophobic regions). Kapton tape or other material may be used as a patterning mask to define the separate regions. The Kapton tape or other material may be applied or deposited, the SEP patterning performed, and then the tape or other material may be removed as necessary. Other SEP treatments may be used depending on the particular substrate materials used, such as for example wet chemical treatments, thin film coating, plasma activation, etc, to define the various regions and/or alter the wetting properties of the treated surfaces.

In step 140, first and second materials are applied on the second region, and in step 150, the first and second materials (e.g., first and second ink materials) are simultaneously doctor blade coated to form first and second material layers on the flexible substrate. It should be noted that steps 140 and 150 may also be simultaneously performed, or separately performed. For example, the first and second materials may be deposited and then the doctor blade may operate to coat the materials to a desired thickness. Alternatively, the first and second materials may be deposited as the doctor blade is moving and forming the material layers. In optional step 160, additional layers may be formed or deposited. For example, additional conductive and intermediary layers may be formed over the formed first and second material layers to improve the device performance. Then the top electrode layer(s) is deposited. Some examples of materials for the top electrode include metals, conductive polymers, conductive oxides, etc.

Embodiments of blade-coating processes for fabricating single color and multicolor OLEDs is schematically shown in FIGS. 1a and 1b, respectively, and the structure of single color and multicolor (red and green in the present example) OLEDs are shown in FIGS. 1c and 1d, respectively. As shown, a blade coater 200 is pushed by an actuator (not shown in the illustration) over the two conductor stripes 210 (e.g., ITO strips formed in step 120). In FIG. 1a, a single ink is used; in FIG. 1b, two different inks are used (red and green inks in the example shown). A small, controllable gap 205 is present underneath the blade of the blade coater 200 that can be used to alter the film thickness of the coated inks by adjusting the height of the gap 205. Prior to ink application, a hydrophobic self-assembled monolayer (SAM) is deposited on the flexible substrate 220 (e.g., 10 cm×10 cm PEN substrate with ITO regions 210), and is surface energy patterned, e.g., patterned using oxygen plasma with a mask made out of Kapton® tape; the desired wetting area is exposed to the oxygen plasma such that the SAM layer is etched off to perform SEP on the substrates. SEP creates hydrophilic areas on the substrate where blade-coated ink adheres to, while the other regions remain hydrophobic. Regions which are hydrophobic after SEP patterning are indicated in FIG. 1b. FIG. 6 shows a comparison between the blade-coating processes with and without the SEP. When coated without the SEP, the ink spreads across the blade, seeping under the blade support at both sides. As a result, more ink is required to print the layer, and the resulting printed film displays poor reproducibility. When using SEP, the coated pattern advantageously remains narrower than the width of the blade support (FIG. 6b, FIGS. 1a, 1b). Hence, the ink is confined by the pattern and leaking through the sides is not observed, which consequently reduces the amount of ink required (e.g., from about 100 µL to about 60 µL), and improves the pattern reproducibility.

Figure 8A:
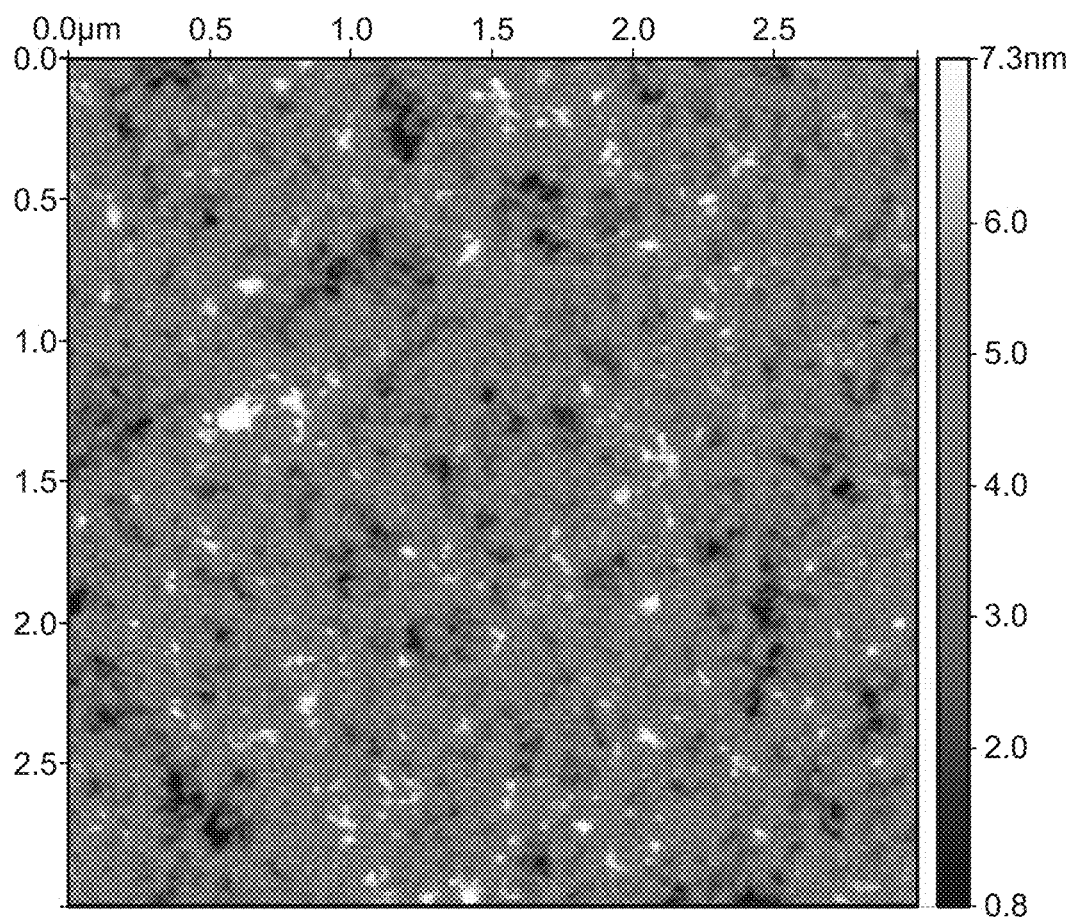
Figure 8B:
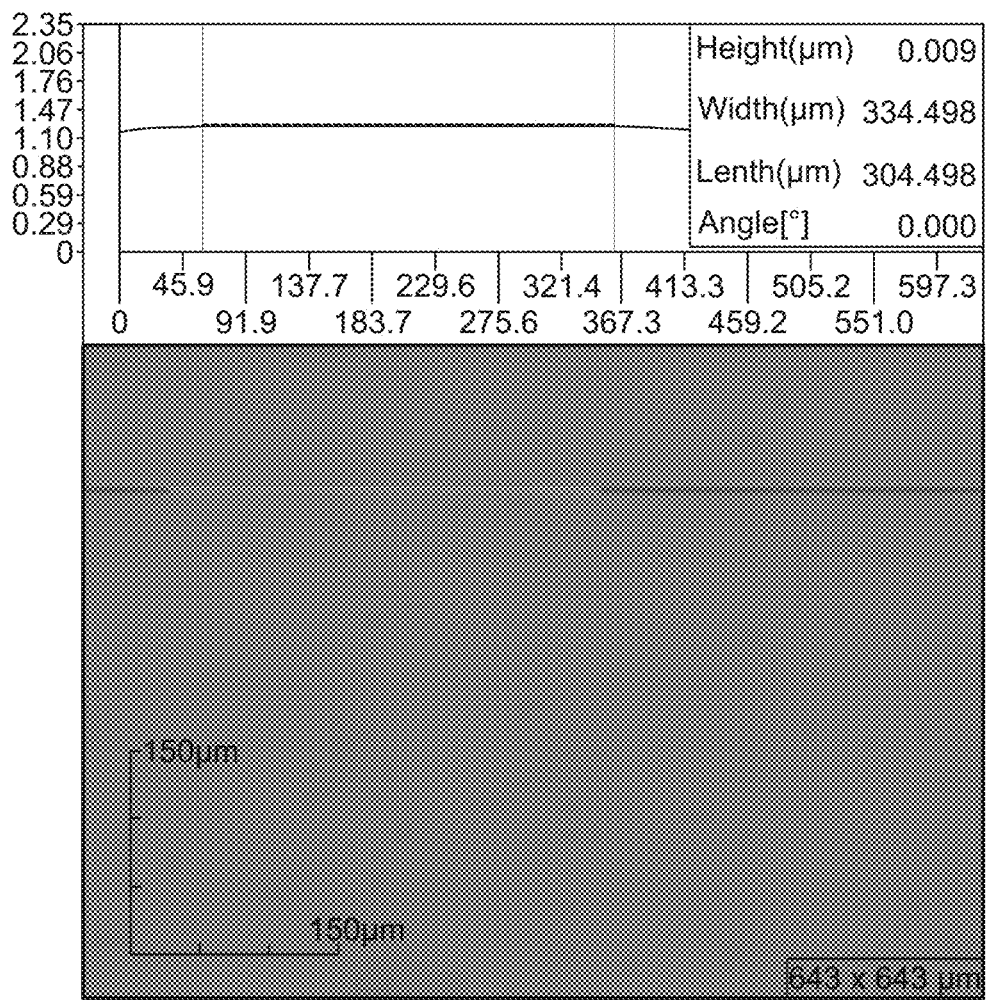
Figure 8C:
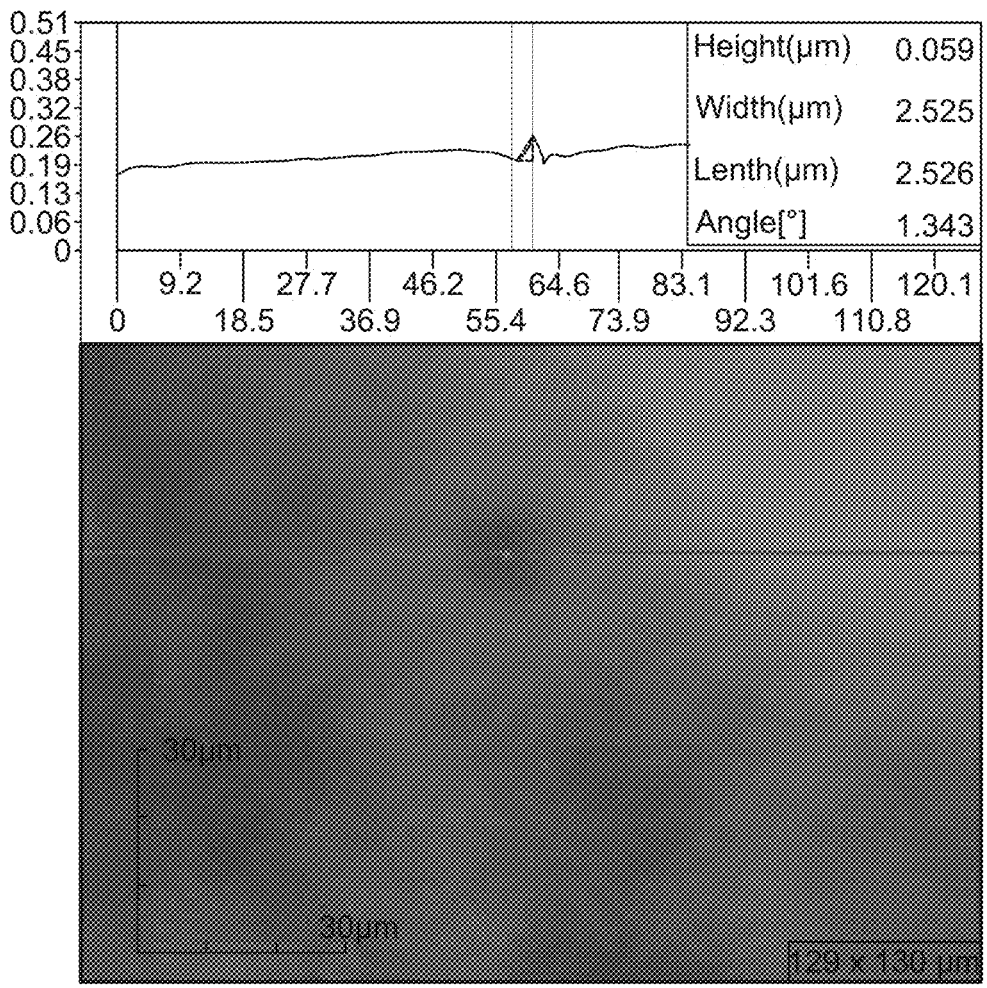
Figure 8D:
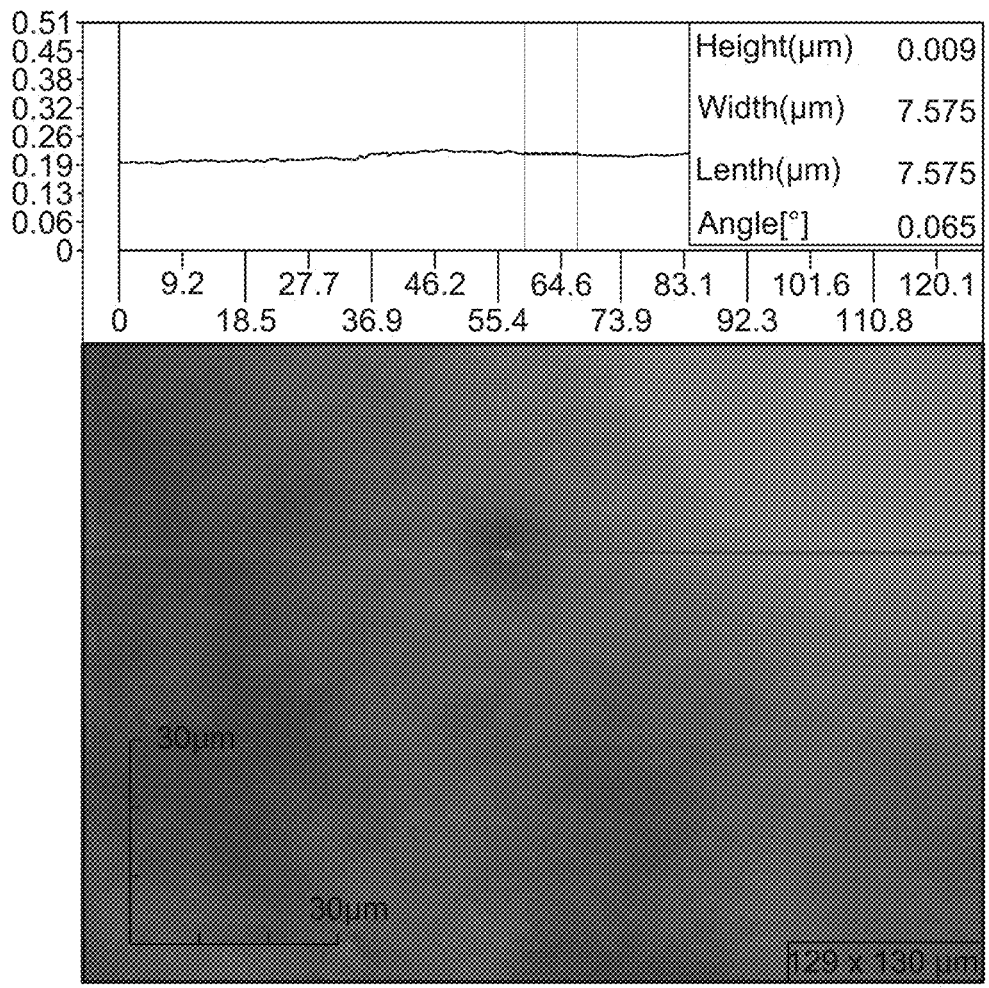

Incorporating SEP in blade coating also advantageously provides a relatively longer uniform printing range (e.g., about 5 cm or more), especially when the target thickness is great, e.g., around 70 nm. While it is possible to achieve reproducible thin (e.g., 20 to 40 nm) Poly(3,4-ethylenedioxythiophene)-poly(styrenesulfonate) (PEDOT:PSS) films without SEP, the blade coating conditions need frequent adjustments, especially for a thicker layer (70 nm) of PEDOT:PSS film, which is attributed to the ink leaking mentioned above. The layer thicknesses show a continuous decrease along the blade coating direction (Table S1). By using SEP, a consistent film thickness is achieved (e.g., a thickness of around 70 nm in an area as large as 5 cm, which is the region 4 to 9 cm away from the reservoir (active region)). The printed film is characterized both along and horizontal to the direction of blade-coating, and was confirmed that the thicknesses in the active region are homogeneous and reproducible as shown in Table S1 and Table S2. In FIGS. 8a and 8b, the film quality is assessed using atomic force microscopy and an optical profilometer, and the peak-to-peak roughness was less than 10 nm for both cases. Within the active region, 3 macroscopic defects or pinholes were observed on average, such as the one shown in FIG. 8c. However, such defects did not have much influence on the roughness near the defect (FIG. 8d) or on the overall film quality. Edge quality of the printed film is shown in FIG. 9. The quality of the edge does not influence the device performance, since the PLED emission area is defined by the overlapping area of the ITO strip and the metal electrode, and films that are blade-coated are wider than the emission area. There are applications where edges need to be well-defined such as OTFTs, where the same printing technique was optimized to make all-printed OTFTs.

As shown in FIG. 1b, for multicolor OLEDs, a thin strip of Kapton® tape is added in between the two ITO strips before plasma etching. The solutions are then delivered separately in front of the blade, at the edges of the two sections divided by the thin Kapton® tape where the blade coating starts. Two different materials can be coated utilizing this separation with a single blade-coat. It should be appreciated that multiple (e.g., more than two) materials may be coated using the present embodiments.

For high-quality and reproducible OLED fabrication on flexible substrates, it is desirable to have the target surface as flat as possible prior to blade coating, especially when working with thickness and roughness sensitive devices such as PLEDs. In one embodiment, polyethylene naphthalate (PEN) is used as the substrate and patterned indium tin oxide (ITO) electrodes as the anode. The PEN/ITO is firmly attached to a carrier (e.g., glass carrier) with Gel-Film (Gel-Pak®). The glass/Gel-Film substrate carrier system is portable and provides a facile way to make a non-rigid substrate flat to make it convenient to handle or process. This system ensures that the substrates are planar and therefore aids a more uniform film to be deposited. One of the challenges when processing on plastic substrates is the fact that deformation at temperatures near the material glass transition temperatures ($T_g$) occurs. This affects the fabrication process, as any slight deformation of the surface adversely affects the quality of the solution-processed film. During the OLED fabrication, annealing (e.g., 180° C. annealing) is required to activate cross-linking of the interlayer in order to allow the subsequent deposition of the emission layer. Using the glass/Gel-Film carrier system the substrate deformation is minimized at the highest temperature used. The samples mounted on the glass carrier with Gel-Film showed no noticeable deformation while the samples with no carrier are noticeably deformed (FIG. 10), increasing the challenge of depositing the subsequent layers.

Figure 2A:
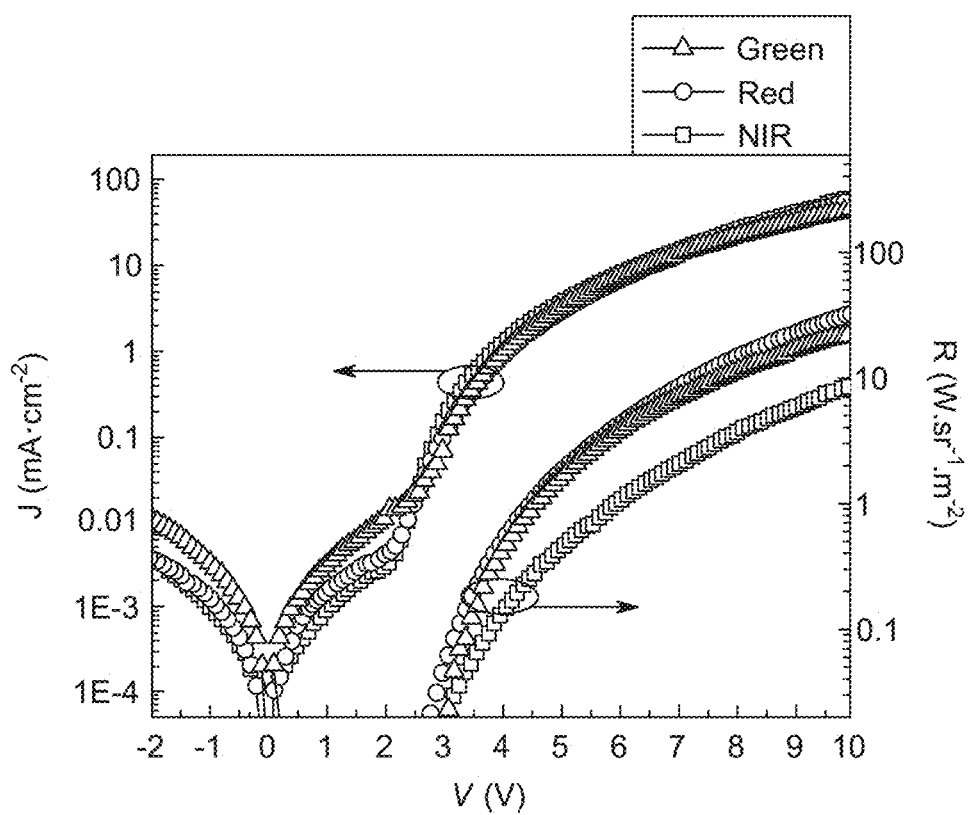

Single color PLEDs with emission in the green, red, and NIR region were fabricated using the SEP technique shown in FIG. 1a. The device characterization of the single color PLEDs is presented in FIG. 2. The current-density-voltageradiance (J-V-R), total flux-J, external quantum efficiency-radiance (EQE-R), and power efficiency-radiance (PE-R) characteristics are shown in FIG. 2a-d, respectively. All devices show a notably clean diode behavior without abnormal discontinuities and have turn-on at less than 3 Volts (V) as seen in the J-V curves (FIG. 2a). Total fluxes reach up to 0.68, 0.89 and 0.19 mW at J=10 mAcm$^{-2}$ from a common emission area of 0.49 cm$^2$, with electroluminescence (EL) peaks at 520, 611 and 725 nm, respectively. At R=1 Wsr$^{-1}$m$^{-2}$, the green PLED operates at 4.6 V, with an EQE of 6.3% and PE of 31.2 mWW$^{-1}$, the red PLED operates at 4.5 V, with an EQE of 10% and PE of 42.7 mWW$^{-1}$, and the NIR PLED operates at 6 V, with an EQE of 3.1% and PE of 8.6 mWW$^{-1}$, respectively. Device operating voltage ($V_{op}$), EQE and PE in mWW$^{-1}$ at R=1 and 10 Wsr$^{-1}$m$^{-2}$ of each color are summarized separately in Table 1.

TABLE 1

Summary of $V_{op}$, EQE and PE of green, red and NIR PLEDs at radiance of 1 and 10 Wsr$^{-1}$m$^{-2}$.

| | @ R = 1 Wsr$^{-1}$m$^{-2}$ | | | @ R = 10 Wsr$^{-1}$m$^{-2}$ | | |
|---|---|---|---|---|---|---|
| | $V_{op}$ (V) | EQE (%) | PE (mWW$^{-1}$) | V (V) | EQE (%) | PE (mWW$^{-1}$) |
| Green | 4.6 | 6.3 | 31.2 | 7.7 | 5.9 | 17.1 |
| Red | 4.5 | 10 | 42.7 | 7.3 | 9.2 | 24.3 |
| NIR | 6 | 3.1 | 8.6 | — | — | — |

These devices show stable characteristics and can provide the expected amount of flux during the course of pulse oximetry measurement. The devices statistically show consistent operating condition in Table S3, which confirms the reproducibility of the devices.

To realize multicolor PLEDs on the same substrate, the SEP technique shown in FIG. 1b was used to fabricate green and red PLEDs on the same substrate. The specific colors are used in order to perform pulse oximetry using PLEDs. Each PLED pixel area is 0.7×0.7 cm$^2$ with 1.7 cm center to center spacing to accommodate a photodiode in between the PLEDs. The device characterization of the multicolor PLEDs is presented in FIG. 3. The current-density-voltage-luminance (J-V-L), total flux-J, external quantum efficiency-L (EQE-L), and luminous efficacy-L (LE-L) plots are shown in FIGS. 3a-d, respectively. A photograph of the multicolor PLEDs is shown in the inset picture of FIG. 3c. Similar to the single color PLEDs shown in FIG. 2, the multicolor PLEDs demonstrate clean J-V characteristics and turns on at less than 3 V. The total flux and the shape of the EL spectra are equivalent to those of the single color PLEDs. At L=1000 cdm$^{-2}$, the green PLED has $V_{op}$ of 6.1 V, EQE of 6.8% and PE of 12.2 lmW$^{-1}$ and the red PLED has $V_{op}$ of 5.8 V, EQE of 11.8% and PE of 8 lmW$^{-1}$. $V_{op}$, EQE, and PE at L=100 and 1000 cdm$^{-2}$ for both colors are summarized in Table 2.

TABLE 2

Summary of $V_{op}$, EQE and PE of green and red PLEDs in multicolor PLEDs at luminance of 100 and 1000 cdm$^{-2}$.

| | @ L = 100 cdm$^{-2}$ | | | @ L = 1000 cdm$^{-2}$ | | |
|---|---|---|---|---|---|---|
| | $V_{op}$ (V) | EQE (%) | LE (lmW$^{-1}$) | V (V) | EQE (%) | LE (lmW$^{-1}$) |
| Green | 4.2 | 7 | 14.2 | 6.1 | 6.8 | 12.2 |
| Red | 3.9 | 11.2 | 9.9 | 5.8 | 11.8 | 8 |

These device characteristics verify that the two different colors are successfully deposited on a single substrate, and the fabricated multicolor PLEDs are as equally stable as the single color PLEDs.

Figure 2B:
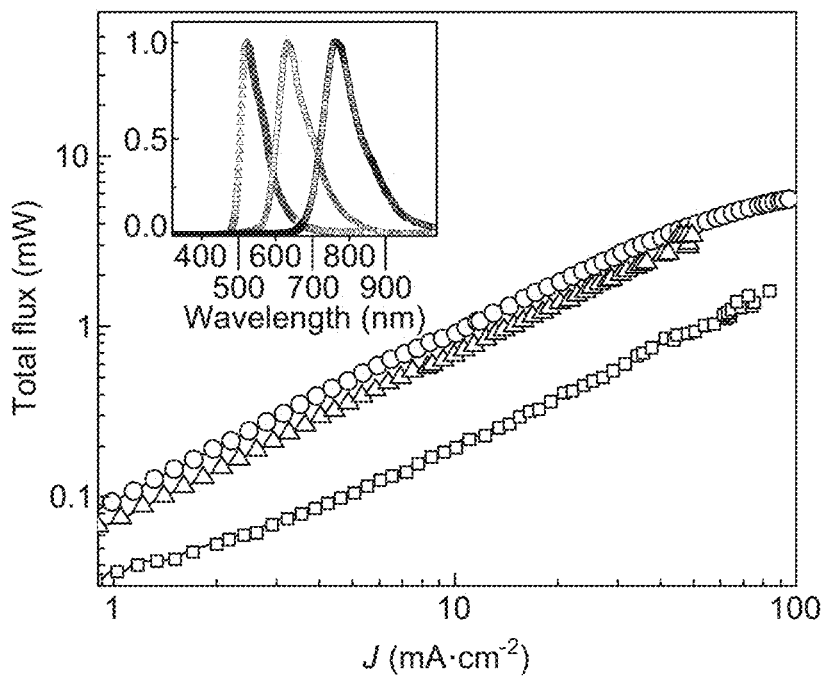
Figure 2C:
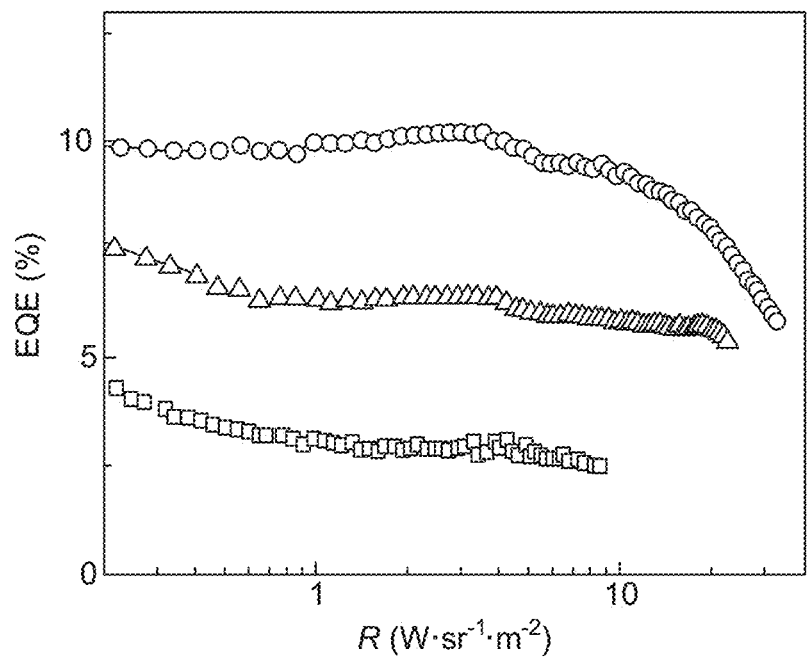
Figure 2D:
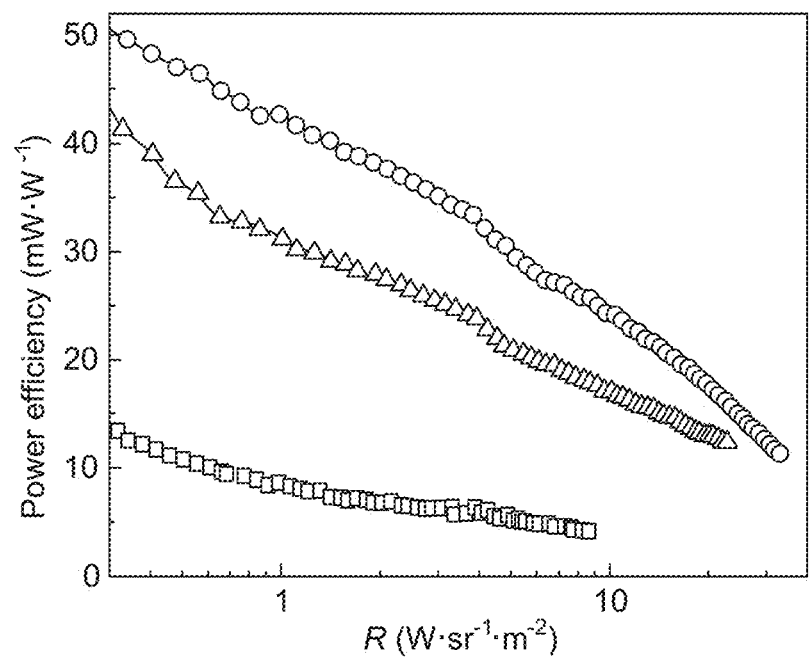
Figure 3A:
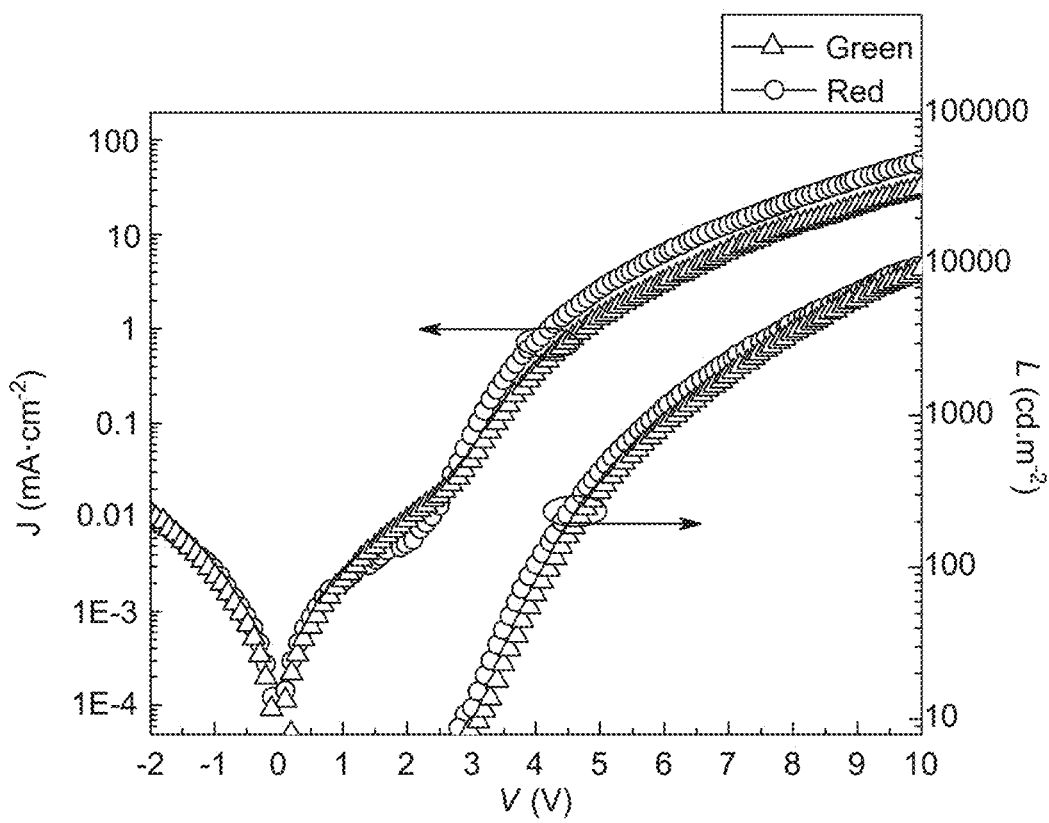
Figure 3B:
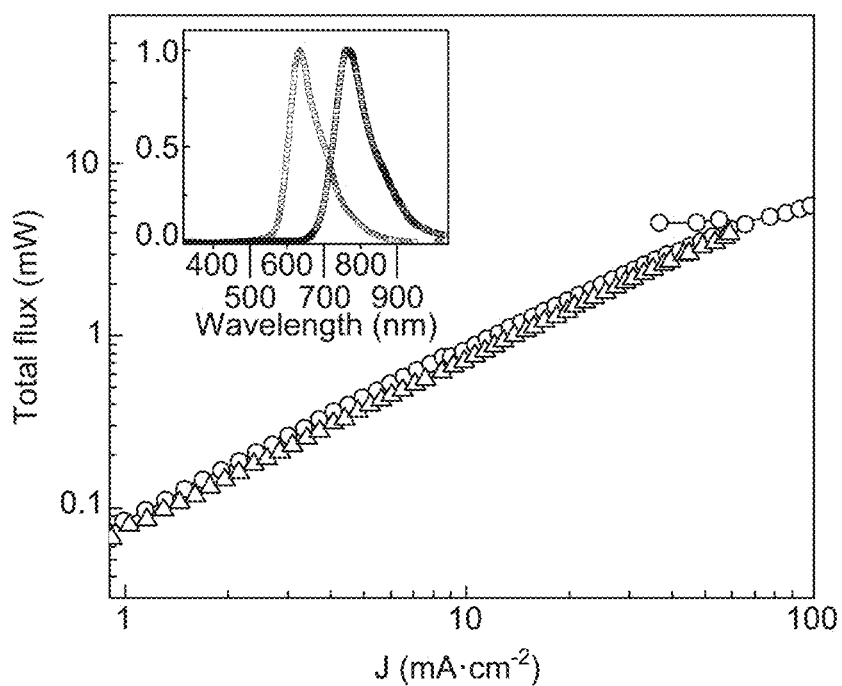
Figure 3C:
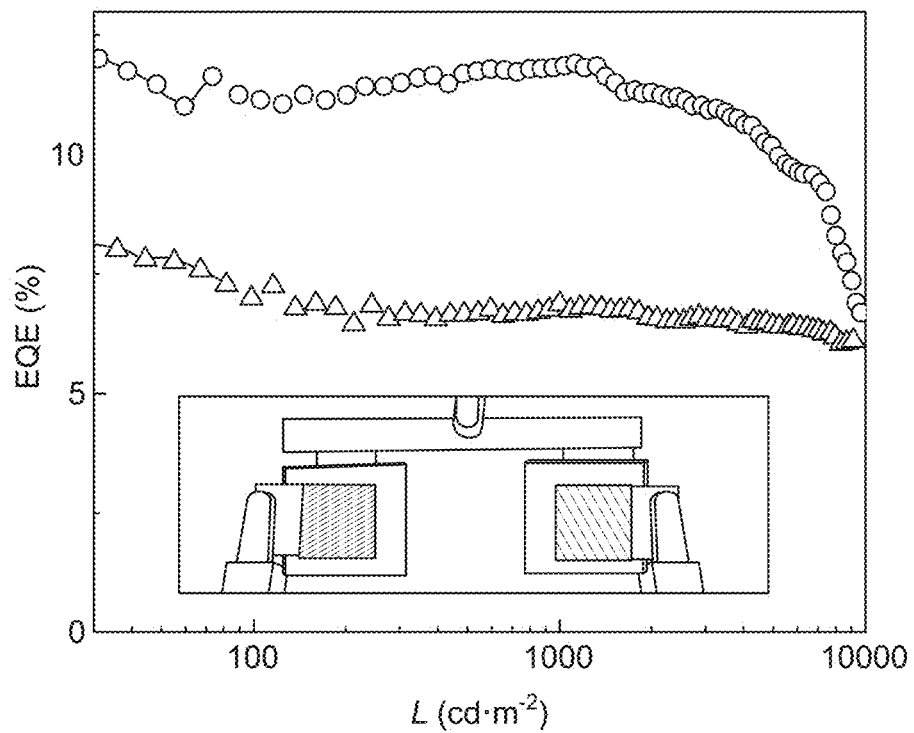
Figure 3D:
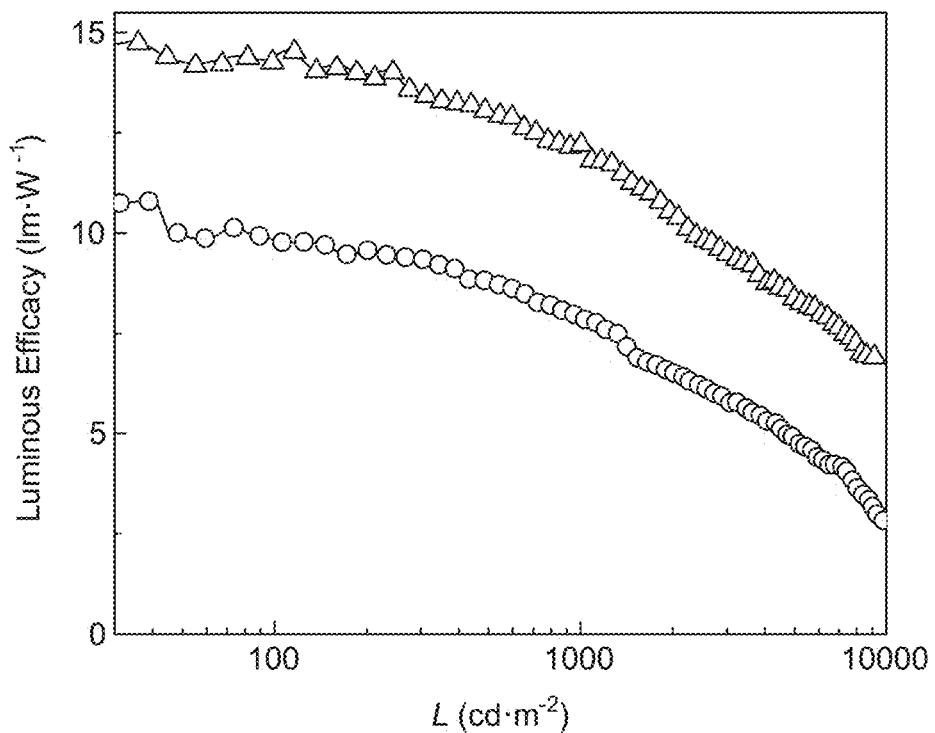
Figure 4A:
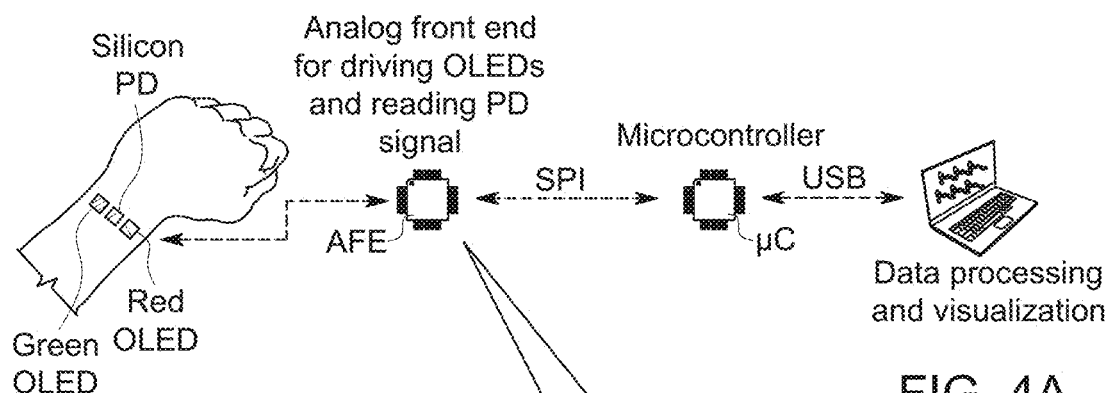
Figure 4B:
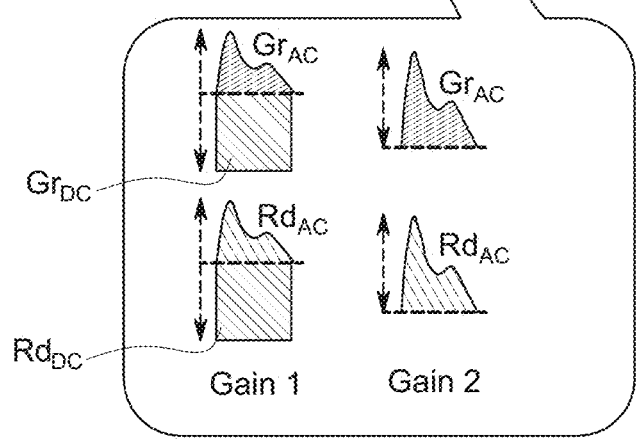
Figure 4C:
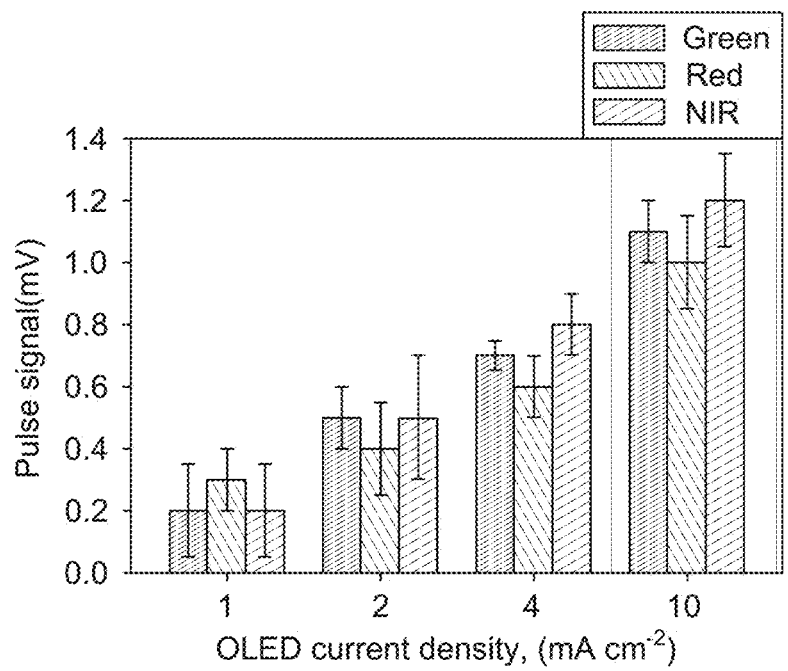
Figure 4D:
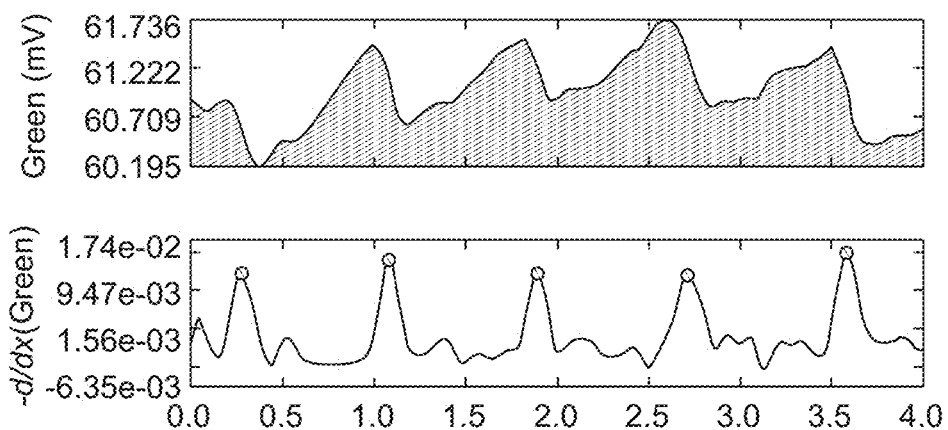
Figure 4E:
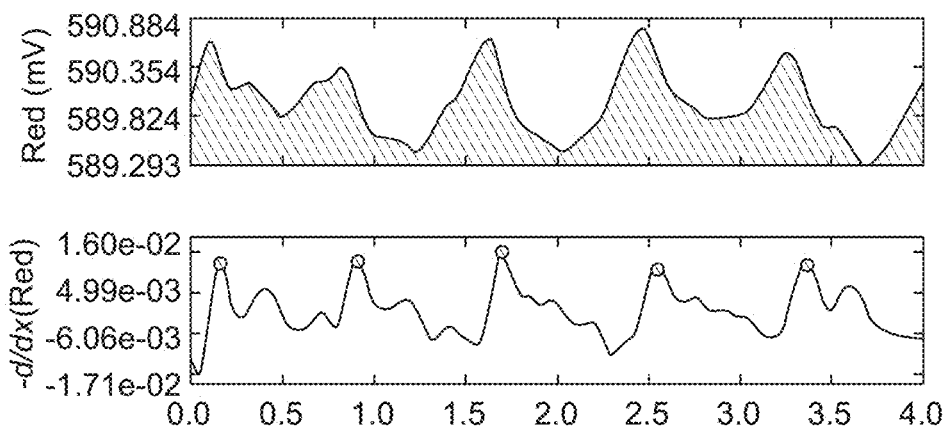
Figure 4F:
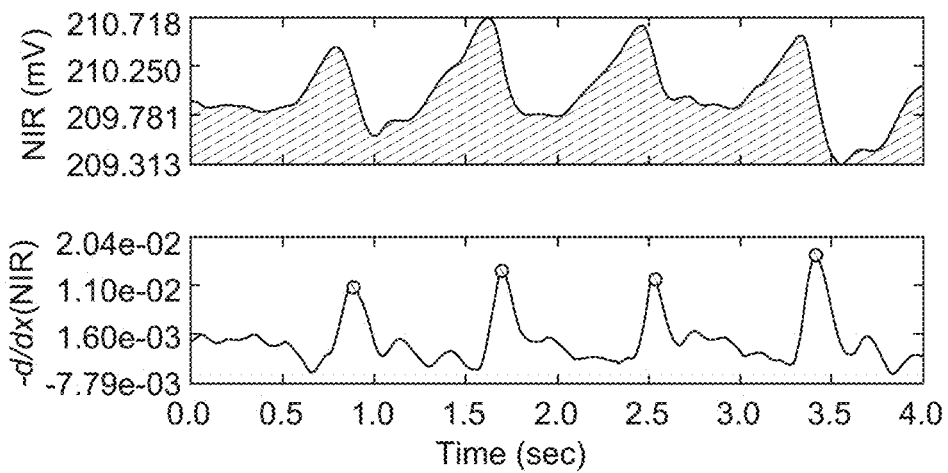

The multicolor PLEDs (green and red) may be used together with a silicon PD to form an optoelectronic sensor that is placed on the wrist. Such an oximetry system is shown in FIG. 4a. The sensor is interfaced with an analog front end (AFE), which drives the PLEDs and reads data from the PD. Two gain stages are used as shown in FIG. 4b—the first gain stage amplifies both the AC and DC part of the PPG signal, and the second gain stage amplifies only the AC part of the signal. The AFE keeps track of the DC level of both the green ($Gr_{DC}$) and red ($Rd_{DC}$) channels as these are used in the pulse oxygenation calculations. The AFE sends out the PPG data to a microcontroller (μC) through a serial peripheral interface (SPI) bus. The signal is sent to a computer using a universal serial bus (USB) for processing and visualization. For applying the multicolor PLEDs as the light source in a reflection-mode pulse oximeter system, the operating conditions of the PLEDs need to be adjusted in a way such that adequate PPG signal levels are obtained during the measurement. Prior to using multicolor PLEDs for the measurement, each single color PLED (e.g., green, red or NIR) and a silicon PD are used to take PPG measurements, which are carried out on a wearer's wrist. This is a typical location where watches or bracelets are worn. To the extent of current knowledge, PPG measurements on the wrist using OLEDs has not been demonstrated yet. The PPG signal intensity on the wrist is significantly smaller than the one measured from the index finger thus more challenging to acquire a strong signal. A series of PPG measurements at different PLED $J_{op}$ using single color PLEDs are evaluated in order to determine the optimum PLED operating conditions for acquiring the PPG signals. The pulse signal magnitudes for the different PLED driving conditions are shown using green, red, and gray colored bars in FIG. 4c. Although it was possible to obtain PPG signals at $J_{op}$ of 1, 2 and 4 mAcm$^{-2}$, low signal intensities hindered the reproducibility of the measurement. The PPG signals measured at 10 mAcm$^{-2}$ were clear and highly reproducible for all the colors (FIGS. 4d-e). Larger signal drift was observed in the case of NIR compared to other colors, however the signal magnitude was highest for the NIR. A peak detection algorithm is used to detect the heart rate from the PPG signals as shown in the bottom panels of FIGS. 4d-e. The PLEDs used for the PPG measurement are immediately characterized again to check the total flux according to J (FIG. 11), which are not different from their initial state (FIG. 2b). By cross-checking this data with the PPG measurement, it is possible to correlate signal magnitude with total flux. 1.1, 1.0, and 1.2 mV PPG signals are obtained using 0.68, 0.89, and 0.19 mW of fluxes, respectively for green, red and NIR PLEDs.

Reflection-mode pulse oximetry was performed using a device including the multicolor PLEDs and a silicon PD. The blade-coated multicolor PLEDs are cut horizontally so that it can be placed on the wrist. The photograph in FIG. 5a shows the configuration of the optoelectronic sensor when placed on the wrist. The oximeter system as described above is used to simultaneously collect the PPG signals from the green and red channels. The signals are shown in FIG. 5b (top two panels). Heartbeat peaks (blue dots) and valleys (red dots) are detected from the PPG signals, and the heart rate (HR) in beats per minute (b.p.m.) by timing the heartbeat peaks is shown in FIG. 5b (black trace). In pulse oximetry, the ratio of the PPG signals are used to calculated the ratio of the PPG signal obtained from two separate channels, $R_{os}=Rd_{AC}/Rd_{DC}/Gr_{AC}/Gr_{DC}$ (FIG. 5b orange trace). The arterial oxygen saturation, $S_aO_2$, is then derived from $R_{os}$ and the molar extinction coefficient of oxy-hemoglobin ($\varepsilon_{\lambda,HbO2}$) and deoxy-hemoglobin ($\varepsilon_{\lambda,Hb}$) at each wavelength:

$$SaO2(Ros)=\varepsilon Rd,Hb-\varepsilon Gr,HbRos/(\varepsilon Rd,Hb-\varepsilon Rd,HbO_2)+(\varepsilon Gr,HbO_2-\varepsilon Gr,Hb)Ros \quad (1)$$

The oxygen saturation $S_pO_2$ (bottom panel of FIG. 5b) is calculated using an empirical correction to Beer-Lambert's law. An average oxygen saturation $S_pO_2$ of 98.77% was recorded which is verified using a commercially available transmission-mode pulse oximeter (FIG. 12).

In conclusion, a surface energy patterning (SEP) technique may be used to fabricate stable and reproducible PLEDs by blade coating. Multiple different colors (e.g., green, red and NIR) may fabricated. The use of SEP greatly improved the reproducibility of the devices, reduced the amount of solution used, and resulted in uniform film thicknesses. By utilizing SEP to coat two (or more) different PLEDs, multicolor blade-coated PLEDs on the same flexible substrate is advantageously realized. As a system-level implementation, multicolor PLEDs (green and red) in conjunction with a silicon photodiode may be used to successfully perform PPG and oxygenation measurements.

Experimental Section

Substrate preparation: 125 μm thick PEN (polyethylene naphthalate) film pre-coated with a 3 μm planarization layer was laminated on 35 cm×35 cm glass carrier substrate using a clear adhesive Gel-Film to give rigidity during processing. A 65 nm Indium Tin Oxide (ITO) layer was deposited via magnetron sputtering in vacuum on top of the substrates which were then patterned using photolithography. The result stack of glass carrier, adhesive, and PEN with patterned ITO are then covered with peelable protection film and scribed to 10 cm×10 cm substrates. The PEN/ITO substrate was rinsed with ethanol before it was baked in the vacuum hotplate at 80° C. overnight. The substrate was taken out in the ambient air and heated up on a hotplate at 180° C. for 30 minutes. Then the substrate was treated with plasma for 10 seconds and entire surface was treated with (heptadecafluoro-1,1,2,2-tetrahydrodecyl)trichlorosilane (FDTS, Gelest SIH5841.0) for 20 minutes under light vacuum (0.1-1 Torr).

Bladecoater setup: A doctor blade (Zehntner ZUA 2000.60) was used to coat PEDOT:PSS (Clevios AI4083, Heraeus), interlayer and the emissive layer. Two linear actuators (Servo City) were set up inside and outside a glovebox, height of which were adjusted to coat on the substrate placed on a hotplate.

Thickness measurement: Substrates were firmly mounted on a glass/Gel-Pak system. A Dektak profiler (Veeco 6M) was used to measure the film thickness.

PLED fabrication: SEP was done by masking the substrate with Kapton® tape before it was plasma treated for 90 seconds. 75 μL of PEDOT:PSS was blade coated with a blade height of 50 μm at 1 cms−1 on a hotplate set to 90° C. The temperature of the hotplate was increased to 130° C. right after blade coating and the substrate was annealed at that temperature for 10 minutes. Then the sample was moved inside the glovebox and interlayer is blade coated with a 50 μL of solution, blade height of 50 μm at 1 cms−1 on a hotplate set to 65° C. After the coat, hotplate was set to 180° C. for 60 minutes. After annealing, the hotplate was set to 65° C. again and the emissive layer was blade coated with 50 μL of solution, 200 μm blade height at 2 cms−1. The film is annealed at 140° C. for 10 minutes. The sample is transferred into a thermal evaporator for deposition of Calcium (99.5%, STREM CHEMICALS) and Aluminum (99.999%, ACI ALLOYS INC).

Device encapsulation: A drop of UV curable epoxy was placed on top of an active pixel and pressed gently with a pre-cut plastic film (PQA1). The sample was placed under UV radiation with a UV lamp (BHK INC.)

Device characterization: The fabricated devices were measured using Keithley 2601 and Keithley 2400 to characterize for J-V and take photodiode readings, respectively. Emission spectra and total flux were measured using Keithley 2601 and a spectrometer (SP-75, Orboptronix) equipped with an integrating sphere.

Reflection-mode oximeter data acquisition, processing, and interpretation: The reflection-mode oximeter system was composed of a Texas Instruments (TI) MSP430 microcontroller (μC) and an analog front end (AFE4490). The AFE controlled the PLEDs and the PD (Hamamatsu S2387-66R), and allowed software control of the PLED drive current and gain parameters of the PD current read circuit. A 100 kΩ resistor (first stage) and 3 dB (second stage) gain were used for amplifying the PD signal. The AFE was interfaced to the μC over serial peripheral interface (SPI) bus, and the final processed signal from the μC was sent to a computer using a universal serial bus (USB). Heart rate was calculated from the PPG signal using a peak detection algorithm and by timing the systolic peaks. Oxygenation was calculated by obtaining the ratio of the red and green PPG signals, Ros=RdAC/RdDC/GrAC/GrDC. Ros was then used to calculate oxygen saturation, SaO2 using an empirical correction to Beer-Lambert's law. Reflection-mode oximetry experiments performed on human subjects were carried out with informed consent under the approval of the University of California, Berkeley Institutional Review Board, protocol ID number 2014-03-6081.

U.S. patent application Ser. No. 15/414,397, filed Jan. 24, 2017 and titled "Reflectance Based Pulse Oximetry Systems and Methods," discloses additional aspects of PPG measurements and useful materials and is hereby incorporated by reference in its entirety for all purposes.

All references, including publications, patent applications, and patents, cited herein are hereby incorporated by reference to the same extent as if each reference were individually and specifically indicated to be incorporated by reference and were set forth in its entirety herein.

The use of the terms "a" and "an" and "the" and "at least one" and similar referents in the context of describing the disclosed subject matter (especially in the context of the following claims) are to be construed to cover both the singular and the plural, unless otherwise indicated herein or clearly contradicted by context. The use of the term "at least one" followed by a list of one or more items (for example, "at least one of A and B") is to be construed to mean one item selected from the listed items (A or B) or any combination of two or more of the listed items (A and B), unless otherwise indicated herein or clearly contradicted by context. The terms "comprising," "having," "including," and "containing" are to be construed as open-ended terms (i.e., meaning "including, but not limited to,") unless otherwise noted. Recitation of ranges of values herein are merely intended to serve as a shorthand method of referring individually to each separate value falling within the range, unless otherwise indicated herein, and each separate value is incorporated into the specification as if it were individually recited herein. All methods described herein can be performed in any suitable order unless otherwise indicated herein or otherwise clearly contradicted by context. The use of any and all examples, or example language (e.g., "such as") provided herein, is intended merely to better illuminate the disclosed subject matter and does not pose a limitation on the scope of the invention unless otherwise claimed. No language in the specification should be construed as indicating any non-claimed element as essential to the practice of the invention.

Certain embodiments are described herein. Variations of those embodiments may become apparent to those of ordinary skill in the art upon reading the foregoing description. The inventors expect skilled artisans to employ such variations as appropriate, and the inventors intend for the embodiments to be practiced otherwise than as specifically described herein. For example, the above methods are also useful for forming different multi-color devices on a rigid substrate. Accordingly, this disclosure includes all modifications and equivalents of the subject matter recited in the claims appended hereto as permitted by applicable law. Moreover, any combination of the above-described elements in all possible variations thereof is encompassed by the disclosure unless otherwise indicated herein or otherwise clearly contradicted by context.

The invention claimed is:

1. A method for simultaneously forming two or more different color material layers on a substrate, the method comprising:
   performing surface energy patterning to define a first region and a second region on the substrate, wherein the first region is hydrophobic and the second region is hydrophilic;
   applying first and second materials on the second region, wherein the first material comprises a material having a first color, and wherein the second material comprises a material having a second color; and
   doctor blade coating the first and second materials simultaneously to form first and second material layers on the substrate.

2. The method according to claim 1, wherein the substrate is a flexible substrate.

3. The method according to claim 1, further including depositing a pattern of a first conductive material on the substrate prior to performing the surface energy patterning.

4. The method of claim 1, wherein the performing surface energy patterning includes:
   applying a hydrophobic self-assembling monolayer (SAM) to the substrate;
   applying an etch barrier material to define a pattern on the SAM;
   etching the SAM to define the first region and the second region; and
   removing the etch barrier material.

5. The method of claim 4, wherein the etch barrier material comprises kapton tape.

6. The method of claim 4, wherein the etching comprises an oxygen plasma etch.

7. The method of claim 2, further including positioning the flexible substrate material on a rigid carrier.

8. The method of claim 1, wherein the applying first and second materials on the second region includes applying the first material on a first portion of the second region and applying the second material on a second portion of the second region different than the first portion of the second region.

9. The method of claim 1, wherein the first and second material layers define first and second organic light-emitting diodes (OLEDs), respectively.

10. The method of claim 2, wherein the flexible substrate comprises polyethylene naphthalate (PEN).

11. The method of claim 3, wherein the first conductive material comprises indium tin oxide (ITO).

12. A method of making multi-color light-emitting devices, the method comprising:
    depositing a pattern of a first conductive material on a flexible substrate;
    performing surface energy patterning to define a first region and a second region on the flexible substrate, wherein the first region is hydrophobic and the second region is hydrophilic;
    applying first and second materials on the second region; and
    doctor blade coating the first and second materials simultaneously to form first and second material layers on the flexible substrate.

13. The method of claim 12, wherein the first and second material layers define first and second organic light-emitting diodes (OLEDs), respectively.

14. The method of claim 12, wherein the flexible substrate comprises polyethylene naphthalate (PEN).

15. The method of claim 12, wherein the first conductive material comprises indium tin oxide (ITO).

16. The method of claim 12, wherein the performing surface energy patterning includes:
    applying a hydrophobic self-assembling monolayer (SAM) to the flexible substrate;
    applying an etch barrier material to define a pattern on the SAM;
    etching the SAM to define the first region and the second region; and
    removing the etch barrier material.

17. The method of claim 16, wherein the etch barrier material comprises kapton tape.

18. The method of claim 16, wherein the etching comprises an oxygen plasma etch.

19. The method of claim 12, further including positioning the flexible substrate material on a rigid carrier prior to the depositing.

20. The method of claim 12, wherein the applying first and second materials on the second region includes applying the first material on a first portion of the second region and applying the second material on a second portion of the second region different than the first portion of the second region.

* * * * *